US007238662B2

(12) United States Patent
Tsai

(10) Patent No.: US 7,238,662 B2
(45) Date of Patent: Jul. 3, 2007

(54) ALPHA 2HS GLYCOPROTEIN FOR TREATMENT OF CANCER AND A METHOD FOR PREPARATION THEREOF

(75) Inventor: David Tsai, Irvine, CA (US)

(73) Assignee: Ambryx Biotechnology, Inc., Riverside, CA (US)

( * ) Notice: Subject to any disclaimer, the term of this patent is extended or adjusted under 35 U.S.C. 154(b) by 467 days.

(21) Appl. No.: 10/267,706

(22) Filed: Oct. 8, 2002

(65) Prior Publication Data

US 2003/0087809 A1 May 8, 2003

Related U.S. Application Data

(63) Continuation-in-part of application No. 10/145,682, filed on May 14, 2002, now Pat. No. 6,720,311, which is a continuation-in-part of application No. 09/902,208, filed on Jul. 9, 2001, now Pat. No. 6,737,402, which is a continuation-in-part of application No. 09/414,136, filed on Oct. 7, 1999, now Pat. No. 6,258,779, which is a continuation-in-part of application No. 09/149,878, filed on Sep. 8, 1998, now Pat. No. 5,994,298, which is a continuation-in-part of application No. 08/993,432, filed on Dec. 18, 1997, now abandoned.

(51) Int. Cl.
*A61K 38/08* (2006.01)
(52) U.S. Cl. .................................. 514/8; 514/2; 514/6
(58) Field of Classification Search ..................... 514/8, 514/2, 6
See application file for complete search history.

(56) References Cited

U.S. PATENT DOCUMENTS

| 5,449,757 | A | | 9/1995 | Serrero |
| 5,500,432 | A | | 3/1996 | Nicolaou |
| 5,550,019 | A | | 8/1996 | Reed |
| 5,591,717 | A | | 1/1997 | Rojiko |
| 5,604,113 | A | | 2/1997 | White |
| 5,624,808 | A | | 4/1997 | Thompson |
| 5,639,727 | A | | 6/1997 | Little et al. |
| 5,650,491 | A | | 7/1997 | Reed |
| 5,656,725 | A | | 8/1997 | Chittenden |
| 5,994,298 | A | * | 11/1999 | Tsai et al. ....................... 514/8 |
| 6,051,401 | A | * | 4/2000 | Chan et al. ................. 435/69.1 |
| 6,946,256 | B1 | * | 9/2005 | McKeon et al. .............. 435/7.1 |
| 2003/0044400 | A1 | * | 3/2003 | Yu ............................ 424/94.1 |

FOREIGN PATENT DOCUMENTS

| WO | WO 86/02651 | 5/1986 |
| WO | 97/31107 | 8/1997 |

OTHER PUBLICATIONS

Yang et al., Molecular Cell, 1998, vol. 2, pp. 305-316.*
Ikawa et al., Jpn. J. Cancer Res., Jun. 1999, vol. 90, pp. 596-599.*
Wang et al., Oncogene, vol. 15 pp. 143-157, Sep. 1997.
Lin, et al., "In Vitro Apoptosis in the Human Hepatoma Cell Line Induced by Transforming Growth Factor $B_1$", Cancer Research, 52, 385-388 (1992).
Grotendorst, et al., "Attachment of Smooth Muscle Cells to Collagen and their Migration toward platelet-derived growth factor", Proc. Natl. Acad. Sci. USA, vol. 78, No. 6, pp. 3669-3672 (1991).
Wiley, et al.. "Identification and Characterization of a new Member of the TNF Family that Induces Apoptosis", Immunity vol. 3, 673-682 (1995).
Kawakami. et al., "Cachectin/TNF Kills or Inhibits the Differentiation of 3T3-L1 Cells According to Developmental Stage", J. of Cellular Physiology 138:1-7 (1989).
Krammer, et al., Apoptosis in the APO-1 system, Apoptosis: The Molecular Basis of Cell Death pp. 87-99 (1991).
von Bulow, et al., "Human fetuin/a,HS glycoprotein in colloid and parenchymal cells in human fetal pituitary gland", Histochemistry, (1993) 99:13-22.
Grant, et al., "Effects of Epidermal Growth Factor, Fibroblast Growth Factor, and Transforming Growth Factor-B on Cornmeal Cell Chemotaxis", Investigative Ophthalmology & Visual Science, vol. 33, No. 12 1992).
Yang, et al., "Human a-HS-glycoprotein/bovine fetuin homologue identification and development regulation of the gene", Biochemica et Biophysica Acta 1130 (1992) 149-156.
Dziegielewska, K.M., et. al., Fetuin, p. 16-17, (R.G. Landes Co.1995).
Dziegielewska, K.M., et. al., Fetuin, "Structure of the Fetuins," Chap. 2, p. 11-42 (R.G. Landes Co.1995).
Yoshioka, et al., The Completer Amino Acid Sequence of the A-chain of Human Plasma a HS-glycoprotein, The Journal of Biological Chemistry, vol. 261, No. 4, pp. 1665-1676 (1986).
Gejyo, et al., "Characterization of the B-Chain of Human Plasma azHS-Glycoprotein", The Journal of Biological Chemistry, vol. 258 No. 8, pp. 4966-4971 (1983).
Kerr, J.F.R. and Searle, J., A Suggested Explanation for the Paradoxically slow growth rate of basal-cell Carcinomas . . . , J. Path., vol. 107, p. 41-44, (1971).
Michaelson, J., Cell Selection in Development, Biol. Rev. (1987), vol. 62, p. 115-139, Great Britain.
Wyllie, A.H., et. al., Cell Death: The Significance of Apoptosis, International Review of Cytology, vol. 68, p. 251-306, Academic Press, 1980.
Cope, F., et. al., Apoptosis: The Molecular Basis of Cell Death, Cold Spring Harbor Laboratory Press, p. 61-86, 1991: Carciogenesis and Apoptosis: Paradigms . . . .
Schmid, K., and Burgi, W. (1961) Biochim. Biophys. Acta 47, 440-453.
Ashton BA, Smith R. Plasma $\alpha_2$-HS glycoprotein concentration in Paget's disease of bone: its possible significance. Clin Sci 1980; 58:435-438.

(Continued)

*Primary Examiner*—Mark L. Shibuya
(74) *Attorney, Agent, or Firm*—Trojan Law Office

(57) ABSTRACT

This invention characterizes the selective apoptotic activity of specially prepared Alpha 2-HS glycoprotein and fragments thereof. Specifically, Alpha 2-HS glycoprotein which has been overloaded with zinc, as well as fragnents thereof, selectively induce apoptosis in HT-29 (colon cancer), LNCaP (prostate cancer) and Hep G2 (hepatoma) cells while having no effect on CCD 18 Co (normal colon) cells.

3 Claims, 11 Drawing Sheets

OTHER PUBLICATIONS

Kalabay L. Cseh K, Benedek S et al. Serum $\alpha_2$-HS glycoprotein concentration in patients with hematological malignancies. A follow-up study. Ann Hematol 1991; 63:264-269.

Schelp FP, Thanangkul O, Supawan V et al. $\alpha_2$-HS-glycoprotein serum levels in protein-energy malnutrition. Br J Nutr 1980; 43:381-383.

Abiodun PO, Ihongbe JC, Dati F. Decreased levels of $\alpha_2$-HS-glycoprotein in children with protein-energy-malnutrition. Eur J Pediatr 1985; 144:368-369.

Abiodun PO, Olomu IN. Serum $\alpha_2$-HS-glycoprotein levels in neonatal infections. Biol Neonate 1991; 60:114-117.

Baskies, et al. "Serum glycoproteins in cancer patients". Cancer, v. 45, pp. 3050-3060 (1980).

Spiro, "Studies on fetuin, a glycoprotein of fetal serum". Journal of Biological Chemistry, v. 235, No. 10, pp. 2860-2869 (1960).

Su, et al. Abstract 1257, FASEB Journal, v. 8, No. 4, p. A218 (1994).

* cited by examiner

| Group | Number of Mice | Dosage | Survivors (days) | Increased Life Span (ILS) |
|---|---|---|---|---|
| I | 10 | 0.002 ml fetuin | 1 (31) | 29% |
| II | 10 | 0.02 ml fetuin | 1 (29) | 17.2 % |
| III | 10 | 0.2 ml fetuin | 8 (58) | 141 % |
| IV | 10 | 0.5 ml saline | 0 (24) | --- |

Fig. 1

| Type of Fetuin | Amount Required to Reach $LD_{50}$ |
|---|---|
| Fetuin + Zn | 130 µM |
| Supercharged Zinc Fetuin | 14.3 µM |

Fig. 2

| Type of Fetuin | Amount Required to Reach $LD_{50}$ |
|---|---|
| Fetuin + Zn | 60 µM |
| Supercharged Zinc Fetuin | 19.6 µM |

| Experiment | Sample | Apoptosis (%) |
|---|---|---|
| 1 | Filtrate (10 µl) | 92% |
|   | Filtrate (10 µl) + proteinase K | 50% |
| 2 | Filtrate (5 µl) | 35% |
|   | Filtrate (5 µl) + proteinase K | 0% |
| 3 | Filtrate (10 µl) | 75% |
|   | Filtrate (10 µl) + proteinase K | 0% |

FIG. 13

| Fetuin | $LD_{50}$ |
|---|---|
| Zinc Charged Fetuin (full length) | $LD_{50}$ = 3-10 µM |
| Fetuin Fragment (amino acid no. 300-309) | $LD_{50}$ = 0.3-0.4 µM |
| Fetuin Fragment (amino acid no. 300-307) | $LD_{50} \gg$ 1 mM |
| Fetuin Fragment (amino acid no. 310-317) | $LD_{50} \gg$ 1 mM |

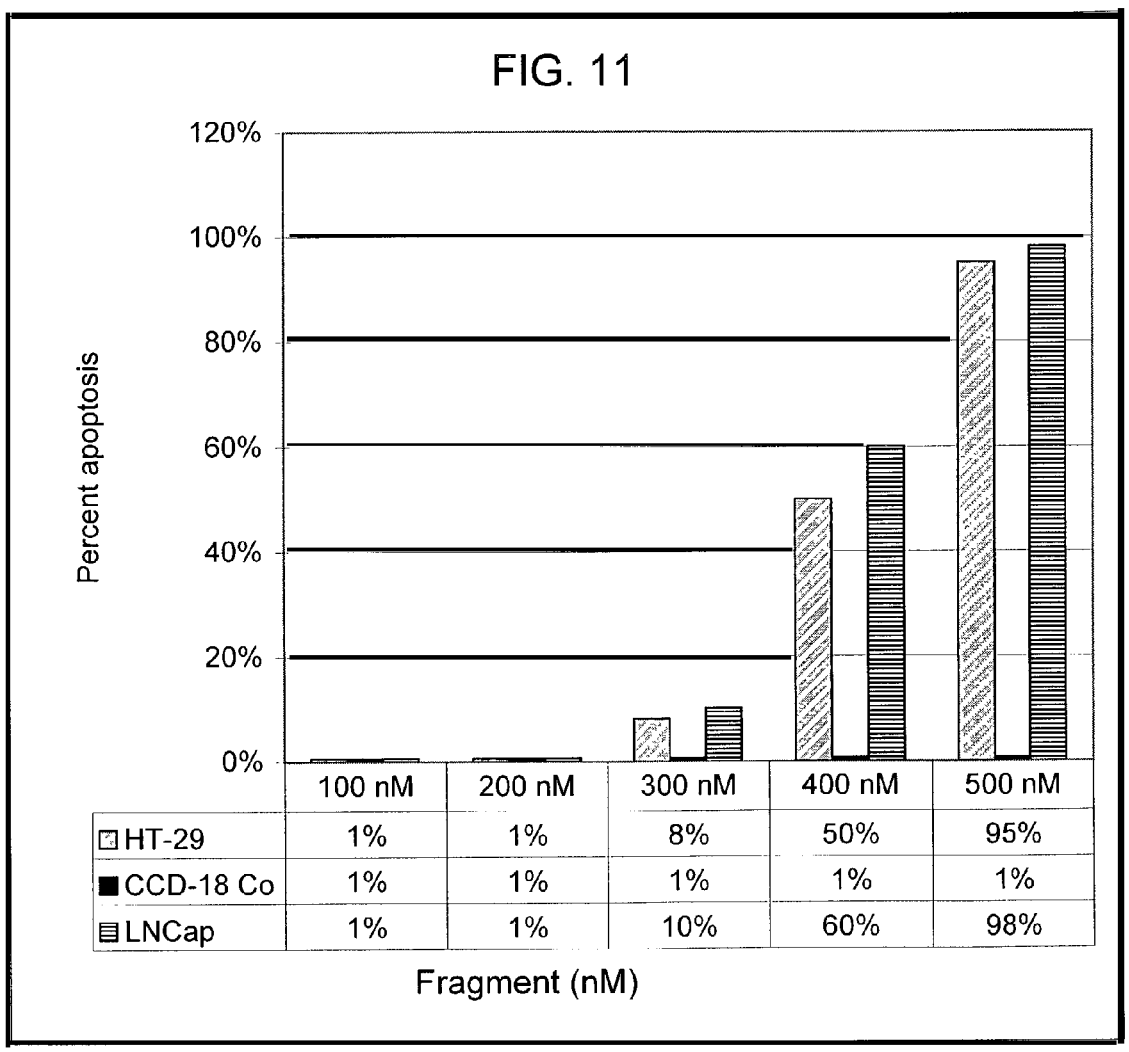

SEQUENCE LISTING

```
<160> NUMBER OF SEQ ID NOS: 7
<210> SEQ ID NO 1
<211> LENGTH: 10
<212> TYPE: PRT
<213> ORGANISM: Bovine
<222> LOCATION: 300..309
<223> OTHER INFORMATION: Polypeptide fragment from treatment of fetuin
      from bovine sera as described in the specification.

<400> SEQUENCE: 1

His Thr Phe Ser Gly Val Ala Ser Val Glu
1               5                   10

<210> SEQ ID NO 2
<211> LENGTH: 8
<212> TYPE: PRT
<213> ORGANISM: Bovine
<222> LOCATION: 311..317
<223> OTHER INFORMATION: Polypeptide fragment from treatment of fetuin
      from bovine sera as described in the specification.

<400> SEQUENCE: 2

Ser Ala Ser Gly Glu Ala Phe His
1               5
```

```
<210> SEQ ID NO 3
<211> LENGTH: 10
<212> TYPE: PRT
<213> ORGANISM: Human
<222> LOCATION: 300..309
<223> OTHER INFORMATION: Polypeptide fragment from fetuin.

<400> SEQUENCE: 3

His Thr Phe Met Gly Val Val Ser Leu Gly
1               5                   10

<210> SEQ ID NO 4
<211> LENGTH: 10
<212> TYPE: PRT
<213> ORGANISM: Pig
<222> LOCATION: 300..309
<223> OTHER INFORMATION: Polypeptide fragment from fetuin.

<400> SEQUENCE: 4

His Ser Phe Ser Gly Val Ala Ser Val Glu
1               5                   10

<210> SEQ ID NO 5
<211> LENGTH: 10
<212> TYPE: PRT
<213> ORGANISM: Sheep
<222> LOCATION: 300..309
<223> OTHER INFORMATION: Polypeptide fragment from fetuin.

<400> SEQUENCE: 5

His Thr Phe Ser Gly Val Ala Ser Val Glu
1               5                   10

<210> SEQ ID NO 6
<211> LENGTH: 10
<212> TYPE: PRT
<213> ORGANISM: Rat
<222> LOCATION: 300..309
<223> OTHER INFORMATION: Polypeptide fragment from fetuin.

<400> SEQUENCE: 6

His Thr Phe Ser Gly Val Ala Ser Val Glu
1               5                   10

<210> SEQ ID NO 7
<211> LENGTH: 10
<212> TYPE: PRT
<213> ORGANISM: Mouse
<222> LOCATION: 300..309
<223> OTHER INFORMATION: Polypeptide fragment from fetuin.

<400> SEQUENCE: 7

His Ala Phe Ser Pro Val Ala Ser Val Glu
1               5                   10
```

US 7,238,662 B2

ALPHA 2HS GLYCOPROTEIN FOR TREATMENT OF CANCER AND A METHOD FOR PREPARATION THEREOF

CLAIM OF PRIORITY

This application is a continuation-in-part to U.S. Ser. No. 10/145,682 (filed 14 May 2002) now U.S. Pat. No. 6,720,311 which is a continuation-in-part to U.S. Ser. No. 09/902,208 (filed 9 Jul. 2001) now U.S. Pat. No. 6,737,402, which is a continuation-in-part to U.S. Ser. No. 09/414,136 (filed 7 Oct. 1999), now U.S. Pat. No. 6,258,779 (issued 10 Jul. 2001), which is a continuation-in-part to U.S. Ser. No. 09/149,878 (filed 8 Sep. 1998), now U.S. Pat. No. 5,994,298 (issued 30 Nov. 1999), which is a continuation-in-part to U.S. Ser. No. 08/993,432 (filed 18 Dec. 1997) now abandoned.

BACKGROUND OF THE INVENTION

Human beings have had a long battle against cancer. Because the disease is so widespread, manifests itself in so many different ways and is so relentless, the potential market for effective cancer therapies is enormous. It is estimated that 10 million people in the U.S. either have or have had cancer. The National Cancer Institute (NCI) projected that in 1995, some 1.2 million new cases of cancer will be diagnosed in the United States, and that 538,000 people will die of the disease.

Cancer is currently treated, with a low degree of success, with combinations of surgery, chemotherapy and radiation. The reason for the low degree of success in chemotherapy is because current chemotherapeutic approaches target rapidly dividing tumor cells. This approach is ineffective against cancer that is dormant or slow growing. Such treatments also affect other, noncancerous cells that divide rapidly, thereby causing harmful side effects.

Recently, a new approach has emerged in the battle against cancer. This approach is based on the biological phenomenon called "Apoptosis". Apoptosis is also called "programmed cell death" or "cell suicide". (Krammer, et al., "Apoptosis in the APO-1 System", Apoptosis: The molecular Basis of Cell Death, pp. 87-99 Cold Spring Harbor Laboratory Press, 1991). In contrast to the cell death caused by cell injury, apoptosis is an active process of gene-directed, cellular self-destruction that serves a biologically meaningful function. (Kerr, J. F. R and J. Searle J. Pathol. 107:41, 1971). One example of the biologically meaningful function of apoptosis occurs during the morphogenesis of an embryo. (Michaelson, J. Biol. Rev. 62:115, 1987). Just as the sculpting of a sculpture needs the addition as well as removal of clay, the organ formation (Morphogenesis) of an embryo relies on cell growth (addition of clay) as well as cell death (removal of clay). As a matter of fact, apoptosis plays a key role in the human body from the early stages of embryonic development through to the inevitable decline associated with old age. (Wyllie, A. H. Int. Rev. Cytol. 68:251, 1980). The normal functioning of the immune, gastrointestinal, and hematopoietic systems depend upon the normal function of apoptosis. When the normal function of apoptosis goes awry, the result can be one of a number of diseases including cancer, viral infections, auto-immune disease/allergies, neurodegeneration, or cardiovascular diseases. Because of the role apoptosis plays in human diseases, apoptosis is becoming a prominent buzzword in the pharmaceutical research field. Huge amounts of time and money are being spent in an attempt to understand how it works, how it can be encouraged or inhibited, and what this means for practical medicine. A handful of companies have been formed with the prime direction of turning work in this nascent field into marketable pharmaceutical products. The emergence of a core of innovative young companies combined with the steps being taken by established industrial players are certain to make apoptosis research one of the fastest-growing and most promising areas of medical study.

The idea that cancer may be caused by insufficient apoptosis first arose in the early 1990's (Cope, F. O. and Wille, J. J., "Apoptosis": The Molecular Basis of Cell Death, Cold Spring Harbor Laboratory Press, p. 61, 1991). This idea opened a door for a new concept in cancer therapy—Cancer cells may be killed by encouraging apoptosis. Apoptosis modulation, based on the processes present in normal development, is a potential mechanism for controlling the growth of tumor cells. Inducing apoptosis in tumor cells is an attractive approach because, at least in theory, it would teach the cells to commit suicide. Nevertheless, since the objective of cancer treatment is to kill cancer cells without killing the host, the success of this treatment is still dependent on the availability of drugs that can selectively induce apoptosis in tumor cells without affecting normal cells. In this patent application, the apoptotic activity of naturally occurring fetuin (which has been modified), chemically synthesized fetuin, recombinant fetuin, and their associated fragments upon cancer cells are elucidated. In addition, the effects of alpha 2 and associated fragments are expounded. These proteins and polypeptides may present a new class of anticancer drugs that induce apoptosis in cancer cells, which may offer a breakthrough in cancer therapy.

SUMMARY OF THE INVENTION

The purpose of this invention is to demonstrate the selective apoptotic activity of fetuin, alpha 2-HS glycoprotein and associated fragments. Specifically, recombinant fetuin from *E. coli* was found to induce apoptotic activity in cancer cells at concentrations of 1 μM. Modified Alpha 2-HS glycoprotein induced apoptosis at $LD_{50}$ (dosage for the induction of 50% cell death) at 6 hours on HT-29, Hep G2, and LNCaP at 0.75 μM, 0.87 μM, and 1.5 μM respectively.

BRIEF DESCRIPTION OF THE DRAWINGS

FIG. 1 shows a table of test data of using fetal fetuin on mice bearing leukemia.

FIG. 2 shows a table of the comparison of original fetuin with zinc in comparison with the supercharged zinc fetuin to reach $LD_{50}$ (dosage for the induction of 50% cell death).

FIG. 3 shows another table of the comparison of original fetuin with zinc in comparison with the supercharged zinc fetuin to reach $LD_{50}$.

FIG. 8 shows a table illustrating, among other things, the effect of incubating the filtrate containing SEQ ID NO: 1 treated with proteinase K.

FIG. 11 is a graph of SEQ ID NO: 1 (nM) versus the percent apoptosis in HT-29, CCD-18 Co, and LNCaP cells.

FIG. 13 is a table of the $LD_{50}$ values for fetuin and various fetuin fragments, including SEQ ID NO: 1.

DETAILED DESCRIPTION OF THE INVENTION

Figure 4:
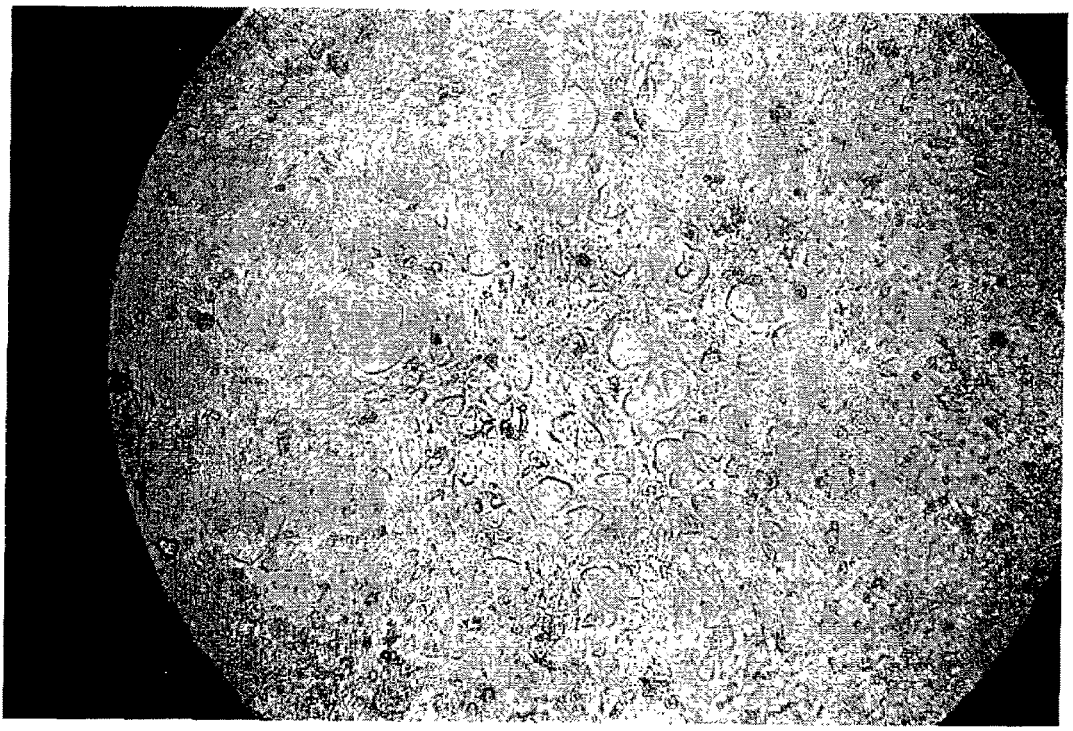
FIG. 4 shows a slide of LNCaP (prostate cancer) cells without treatment of filtrate containing SEQ ID NO: 1.

Initially, five proteins were isolated: Apogen P-1a, Apogen 1b, Apogen 1c, Apogen P-2 and Apogen L.

(A) Isolation of Apogen P-1

(1) Source of Apogen P-1

Apogen P-1 was isolated from the conditioned medium of a cell line called XC, which was derived from rat tumor (ATCC CCL 165). XC cells were first grown in Dulbecco's Modification of Eagle's Medium (DMEM) containing 10% Fetal bovine serum (FBS) for 3 days. XC cells were then washed with PBS (3×100 ml) to remove serum and then grown in DMEM containing no FBS for 4 days. From this serum free conditioned medium, an activity inducing apoptosis in a prostate cancer cell line called LNCAP was detected. On the other hand, normal human lung fibroblast cell line (CCD 39 Lu) and breast cancer cells (MCF-7) were not affected by this activity.

(2) Activity of Apogen P-1

(a) Apoptosis Inducing Activity

The activity of the crude conditioned medium of XC cells was tested on the following cell lines: JEG-3 (Choriocarcinoma), G401 (Wilm's tumor) LNCAP (Prostate cancer), T84 (colon cancer), HL-60 (leukemia), breast cancer cells (MCF-7), and CCD 39 Lu (normal lung fibroblast). When 10 folds concentrated conditioned medium was incubated for 18 hours with the above cell lines in the presence of 5% serum, the conditioned medium induced apoptosis in JEG-3 cells (35%), G 401 cell (27%), LNCaP(100%) and without activity in CCD 39 Lu (0%), T84(0%), MCF-7(0%) and HL-60(0%).

Apoptosis is a distinct type of cell death that differs fundamentally from degenerative death or necrosis in its nature and biological significance. A cell undergoing apoptosis is distinct from a cell undergoing necrosis both morphologically and biochemically. Morphologically, the earliest definitive changes in apoptosis that have been detected with the electron microscope are compaction of the nuclear chromatin into sharply circumscribed, uniformly dense masses about the nuclear envelope and condensation of the cytoplasms. Phase-contrast microscopy of cells under apoptosis shows the condensation and the fragmentation of DNA and the blebbing of the cell.

To morphologically demonstrate that the XC conditioned medium contains activity inducing apoptosis, LNCAP cells were incubated with control medium or the conditioned medium treated as described as above for 15 hr and then stained with Hoechst dye for 2 hours. The nuclei of the LNCAP cells that had been incubated with the control medium were normal and healthy. However, the nuclei of the LNCAP cells that had been incubated with the conditioned medium (X20, exchanged to RPMI) showed the characteristics of apoptosis. First, the conditioned medium caused the condensation of the nucleus, demonstrated by the more intense fluorescent light compared with the control nucleus. Second, the nucleus condensation was accompanied by the fragmentation of DNA, as demonstrated by the breakage of the nucleus. As mentioned above, the condensation of the nucleus and the DNA fragmentation are the morphological characteristics of cells under apoptosis. These results suggest that the conditioned medium from XC cells contain an activity inducing apoptosis in LNCAP cells. On the other hand, the conditioned medium fails to induce apoptosis in normal human lung fibroblast (CCD 39 Lu cells) and breast cancer cells (MCF-7). The nuclei of CCD 39 Lu cells remain the same with or without incubating with the conditioned medium of XC cells Such an apoptosis assay has been used to pre-select proteins and protein fragments for having apoptotic activity on cancer cells.

(b) Cell Repelling Activity

The partially purified Apogen P-1b (Q2 anionic exchanger chromatography step) isolated as described below was recently found to contain an activity other than inducing apoptosis. It was found that Apogen P-1b has an activity that repels cells away. This activity is opposite to that of growth factors; many growth factors such as Platelet Derived Growth Factor (PDGF), Epidermal Growth factor (EGF), Fibroblast Growth factor (FGF) or Transforming Growth factor (TGF) function as a "chemoattractant"—which means that these growth factors attract cells toward them. (Grotendorst, G. R. et al., Proc. Natl. Acad. Sci. 78:3669, 1981; Grant, M. B. et al Invest. Ophthal. Visual Science. 33:3292, 1992). This finding suggests that Apogen P-1b isolated in this invention plays an opposite biological function as that of a growth factor. That is, growth factors induce cell growth and attract cells, whereas Apogen P-1b induces cell death and repels cells. Apogen P-1b is the first "chemorepellent" found in the field of modern biology.

A tissue culture device called Transwell Insert purchased from Costar (Cambridge, Mass.) was used to discover the chemorepellent activity of Apogen P-1b. This device, which has been widely used for the studies of cell migration/invasion, contains an upper chamber and a lower chamber. Between these two chambers is a polyester microporous membrane with 3.0 μm pore size, which allows cells to migrate through the membrane. Tested cells are grown on the upper chamber, and the tested compound is placed in the lower chamber. If this tested compound is a chemoattractant, more cells should migrate through the membrane than the control sample. In our experiments, Hep G2 (100,000 cells) cells, which have a cell size 3-4 times as big as the membrane pore size, were grown in the upper chamber for 2 hours, and then, the partially purified Apogen-1b (30 μl) isolated by ammonium sulfate precipitation and Q2 HPLC chromatography as described above was placed in the lower chamber. After 15 hours, cells that had migrated through the membrane were collected by treating the membrane with 0.2 ml of trypsin solution for 30 min. Cells in ten microliters of the trypsin solution were counted in a hemacytometer. In several experiments, it was found that the partially purified Apogen-1b contained an activity decreasing the number of cells going through the membrane. For example, in one experiment, in the presence of the partially purified Apogen P-1b, the cell number in 10 microliters trypsin solution (which are the cells go through membrane) is 24+−4, whereas the number of cells that go through the membrane in the control experiment is 82+−27. This result suggests that the partially purified Apogen P-1b prevents Hep G2 cells from migrating through membrane. To unequivocally show that Apogen P-1b repel cells, an inverted experiment was installed. Instead of placing Apogen P-1b in the lower chamber, Apogen P-1b was placed in the upper chamber. After 12 hours, 56+−19 cells went through the membrane compared with the control experiment of 30+−1.7 cells per 10 microliters of trypsin solution. The statistically significant increase or decrease in the number of cells going through the membrane by alternatively placing Apogen P-1b in the upper or lower chamber of this tissue culture device strongly suggests that Apogen P-1b repels cells.

(3) Isolation of Apogen P-1 from XC Conditioned Medium

The Apogen P-1 present in the conditioned medium was isolated by the following steps:

Step 1: Ammonium Sulfate Precipitation

Apogen P-1 was precipitated by 80% saturated of ammonium sulfate by adding 561 g of ammonium sulfate per liter of conditioned medium. Pellet was collected by centrifugation and the proteins were dissolved in 10 mM Tris-HCl (pH 7.4). After removal of ammonium sulfate by dialysis, the dissolved proteins were separated by a Q2 HPLC column.

Step 2: Q2 HPLC Chromatography

The dissolved proteins isolated by ammonium sulfate precipitation were concentrated and loaded on to a Q2 column (Bio-Rad) which was further developed by a linear gradient constructed by buffer A (10 mM Tris-HCl, pH 7.4) and buffer B (10 mM Tris-HCl, pH 7.4, 0.55 M NaCl) using BioRad's BioLogic HPLC system. The linear gradient was constructed by increasing buffer B from 0% to 100% in buffer A within 10 min (20 milliliter elution volume) and thereafter the column was eluted with 100% buffer B for 5 min.

The Apogen P-1 activity was assayed by the induction of apoptosis in LNCAP cells. We found that there were three activity peaks across the chromatogram profile. Fraction 5 to 7 caused 70% cell death; fraction 8-10 caused 65% cell death; and fraction 11-14 caused 90% cell death in 18 hr. We collected fractions 5-7 and named it Apogen P-1a; fractions 8-10 was named Apogen P-1b; and fractions 11 to 14 was named Apogen P-1c. These three Apogen P-1's were further purified by a reverse phase column.

Step 3: Reverse Phase Chromatography.

Apogen P-1a, Apogen P-1b and Apogen P-1c were separately concentrated to 1.5 ml. One ml of methanol containing 0.05% trifluoracetic acid was added. In each sample, a large amount of protein was precipitated by this treatment. Whereas, the apoptosis inducing activity remained in the supernatant. The supernatant was then applied to a reverse phase RP-4 column (Micra Scientific Inc) and developed by a linear gradient constructed by solution A (H2O, 0.05% TFA) and solution B (Methanol, 0.05% TFA). The linear gradient was constructed by increasing solution B from 0% to 100% in solution A within 10 min (20 milliliter elution volume) and thereafter the column was eluted with 100% solution B for 5 min.

Step 4: Preparative Electrophoresis.

Apogen 1c isolated by anion exchange chromatography was purified by both Reverse phase chromatography (step 3) and Preparative Electrophoresis by a MiniPrep Gel electrophoresis (Bio-Rad). In the reverse phase chromatogram of Apogen P-1a, fractions 12-13 had activity inducing 80% cell death in LNCAP cells at 10 hr. In the reverse phase chromatogram of Apogen P-1b, fractions 14 and 15 had activity inducing 45% cell death in LNCAP cells at 18 hr.

In the reverse phase chromatogram of Apogen P-1c, fraction No. 5 had activity inducing 52% cell death in LNCAP cells at 18 hr.

The purity of the isolated Apogen P-1a, Apogen P-1b and Apogen P-1c was checked with SDS-polyacrylamide gel electrophoresis stained with silver staining.

(1) Apogen P-1a: a protein band with molecular weight of 70 KD was obtained. This result suggests the successful purification of Apogen P-1a, which has the molecular weight of 70 KD on SDS-PAGE.

(2) Apogen P-1b: A single faint protein band with molecular weight of 55 KD was obtained. This result suggests the successful purification of Apogen P-1b, which has the molecular weight of 55 KD on SDS-PAGE.

(3) Apogen P-1c: The purification of Apogen 1c by Reverse Phase chromatography leads to the isolation of a 70 KD protein whereas the purification of Apogen-1c by preparative electrophoresis leads to the purification of a 57 KD protein. A major protein band with molecular weight of 70 KD was obtained by Reverse Phase chromatography. A 57 KD protein, on the other hand, was isolated by preparative electrophoresis.

The next obvious step would be to obtain enough of the protein band to sequence it.

(B) Isolation of Apogen P-2

(1) Source of Apogen P-2

Apogen P-2 was isolated from the conditioned medium of a cell line called C3H 10T1/2, which was derived from mouse embryo cells (ATCC CCL 226). C3H 10T1/2 cells were first grown in alpha Modification of Eagle's Medium (alpha-MEM) containing 10% Fetal bovine serum (FBS) for 3 days. Cells were then washed with PBS (3×100 ml) to remove serum and then grown in alpha-MEM containing no FBS for 4 days. From this serum free conditioned medium, we detected an activity inducing apoptosis in a prostate cancer cell line called LNCAP. On the other hand, normal human lung fibroblast cell line (CCD 39 Lu) was not affected by this activity.

(2) Activity of Apogen P-2

(a) Apoptosis Inducing Activity

The activity of the crude conditioned medium of C3H 10T1/2 cells was tested on the following cell lines: LNCAP (Prostate cancer), breast cancer cells (MCF-7), and CCD 39 Lu (normal lung fibroblast). When the 10-fold concentrated conditioned medium was incubated for 18 hours with the above cell lines in the presence of 5% serum, the conditioned medium induced apoptosis in LNCaP (100%) and without activity in CCD 39 Lu (0%). To morphologically demonstrate that the C3H 10T1/2 conditioned medium contains activity inducing apoptosis, LNCAP cells were incubated with control medium or with the conditioned medium treated as described as above for 15 hr and then stained with Hoechst dye for 2 hours. The nuclei of the LNCAP cells that had been incubated with control medium were normal and healthy. However, the nuclei of the LNCAP cells that had been incubated with the conditioned medium showed the characteristic of apoptosis. First, the conditioned medium caused the condensation of the nucleus as demonstrated by the more intense fluorescent light compared with the control nucleus. Second, the condensation of the nucleus was accompanied by the fragmentation of DNA as demonstrated by breakage of the nucleus. As mentioned above, the condensation of the nucleus and DNA fragmentation are the morphological characteristics of cells under apoptosis. The same holds true of breast cancer cells (MCF-7) in which 85% apoptotic effect was observed after 18 hours of exposure to P-2. These results suggest that the conditioned medium from C3H10T1/2 cells contains an activity inducing apoptosis in LNCAP and MCF-7 cells. On the other hand, the conditioned medium failed to induce apoptosis in normal human lung fibroblast (CCD 39 Lu cells). The nuclei of CCD 39 Lu cells remained the same with or without incubating with the conditioned medium of C3H10T1/2 cells.

(b) Cell Repelling Activity

The partially purified Apogen P-2, isolated by ammonium sulfate precipitation, hydroxylapatite, and heparin treatment as described above, was recently found to contain an activity other than inducing apoptosis. Similar to Apogen P-1b, Apogen P-2 has activity that repels cells away. Transwell Insert purchased from Costar (Cambridge, Mass.) was used to discover the chemorepellent activity of Apogen P-2. This device, which has been widely used for the study of cell migration/invasion, contains an upper chamber and a lower chamber. Between these two chambers is a polyester microporous membrane with 3.0 µm pore size, which allows the cells to migrate through the membrane. The tested cells (HL-60) were grown on the upper chamber, and the tested compound (Apogen P-2) was placed in the lower chamber. In our experiments, HL-60 (100,000 cells) cells, which have a cell size 2-3 times as big as the membrane pore size, were grown in the upper chamber for 2 hours, and then, the partially purified Apogen P-2 (30 µl) isolated by ammonium sulfate precipitation, hydroxylapatite, and Heparin agarose as described above was placed in the lower chamber. After 6 hours, cells that had migrated through the membrane were collected from the lower chamber; the medium in lower chamber (0.6 ml) was centrifuged for 10 min; and the HL-60 cells that went through the membrane were collected and resuspended in 80 µl of PBS. The cells in ten microliters of the PBS solution were counted in a hemacytometer. In several experiments, we found that the partially purified Apogen P-2 contained an activity that decreased the number of cells going through the membrane. For example, in one experiment, in the presence of the partially purified Apogen P-2, the number of cells in 10 microliters PBS solution (which are the cells that pass through the membrane) was 47+−5.6, whereas the number of cells that went through the membrane in the control experiment was 213+−40. At this moment, no apoptosis was observed in HL-60 cells present in the upper chamber. This result suggests that the partially purified Apogen P-2 prevents the HL-60 cells from migrating through membrane.

(3) Isolation of Apogen P-2 from C3H10T1/2 Conditioned Medium

The Apogen P-2 present in the conditioned medium was isolated by the following steps:

Step 1: Ammonium Sulfate Precipitation.

Apogen P-2 was precipitated by ammonium sulfate (80% saturated) by adding 561 g of ammonium sulfate per liter of conditioned medium. The pellet was collected by centrifugation, and the proteins were dissolved in 10 mM Tris-HCl (pH 7.4).

Step 2: Hydroxylapatite Treatment.

After removal of ammonium sulfate by dialysis in 10 mM Tris-HCl (pH 7.5), the dissolved proteins were incubated with Hydroxylapatite gel (Bio-Gel HTP gel, Bio-Rad) for 1 hr. After removing HTP gel by centrifugation, the activity inducing apoptosis in LNCAP cells was found to be present in the supernatant, which was then further treated with Heparin agarose gel.

Step 3: Heparin Agarose Treatment.

The supernatant from step 2 was further incubated with Heparin agarose (Sigma) for 1 Hr. After removing HTP gel by centrifugation, the activity inducing apoptosis in LNCAP cells was found to be present in the supernatant.

Step 4: Reverse Phase Chromatography.

Apogen P-2 present in the supernatant of Heparin agarose in step 3 was further purified by reverse phase chromatography. Apogen P-2 was concentrated to 1 ml. One milliliter of methanol containing 0.05% Trifluoracetic acid was added. A large amount of protein was precipitated by this treatment. Whereas, the apoptosis inducing activity (P-2) remained in the supernatant. The supernatant was then applied to a reverse phase RP-4 column (Micra Scientific Inc) and developed by a linear gradient constructed by solution A ($H_2O$, 0.05% TFA) and solution B (Methanol, 0.05% TFA). The linear gradient was constructed by increasing solution B from 0% to 100% in solution A in 10 min (20 milliliter elution volume) and thereafter the column was eluted with 100% solution B for 5 min.

In the reverse phase chromatogram of Apogen P-2, fractions 12-14 have activity inducing 80% cell death in LNCAP cells at 12 hr. The purity of the isolated Apogen P-2 was checked with SDS-polyacrylamide gel electrophoresis stained with silver staining, and a single protein band with molecular weight of 65 Kd was obtained.

(C) Isolation of Apogen L (1) Source of Apogen L

Apogen L was isolated from the conditioned medium of XC cell line (ATCC CCL 165). XC cells were grown in Dulbecco's Modification of Eagle's Medium (DMEM) containing 10% Fetal bovine serum (FBS) for 4 days. From this conditioned medium, we detected an activity inducing apoptosis in a leukemia cell line called HL-60. On the other hand, normal human lung fibroblast cell line (CCD 39 Lu) was not affected by this activity.

(2) Isolation of Apogen L from XC Conditioned Medium

The Apogen L present in the conditioned medium was isolated by the following steps:

Step 1: DE52 Absorption

The conditioned medium was incubated with the anion exchanger, DE 52 (Diethylaminoethyl cellulose, Whatman) for 1 hr. The incubation mixture was centrifuged and DE 52, which binds Apogen L was collected and washed with 10 mM Tris-HCl (pH 7.5) containing 0.15 M NaCl. Apogen L was then eluted from DE 52 cellulose by 10 mM Tris-HCl (pH 7.5) containing 0.5 M NaCl.

Step 2: Heparin Agarose Absorption

Apogen L isolated as described in step 1 was further absorbed by Heparin agarose (Sigma) by incubating Apogen L with Heparin agarose for 1 hr. Heparin agarose was collected by centrifugation and was washed with 10 mM Tris-HCl (pH 7.5). Apogen L absorbed in Heparin agarose was then eluted by 2 M NaCl.

Step 3: Q2 HPLC Chromatography

Apogen L isolated as described above was concentrated and loaded onto a Q2 column (Bio Rad) which is further developed by a linear gradient constructed by buffer A (10 mM Tris-HCl, pH 7.4) and buffer B (10 mM Tris-HCl, pH 7.4, 0.5 M NaCl) using Bio-Rad's BioLogic HPLC system. The linear gradient was constructed by increasing buffer B from 0% to 100% in buffer A within 10 min. The purity of the isolated Apogen L was checked with SDS-polyacrylamide gel electrophoresis stained with silver staining. A single protein band with molecular weight of 55 Kd was obtained.

(3) Activity of Apogen L

The activity of Apogen L isolated as described above was tested on the following cell lines: HL-60 (leukemia) and CCD 39 Lu (normal lung fibroblast). To morphologically demonstrate that Apogen L contains activity inducing apoptosis, HL-60 cells were incubated with Apogen L isolated as described above for 15 hr and then stained with Hoechst dye for 2 hours. The nuclei of the HL-60 cells that had been incubated with control medium were normal and healthy. However, the nuclei of the HL-60 cells that had been incubated with Apogen L showed the characteristic of apoptosis. First, Apogen L caused the condensation of nucleus as demonstrated by the more intense fluorescent light compared with the control nucleus. Second, the nucleus condensation was accompanied by the fragmentation of DNA as demonstrated by the breakage of nucleus. As mentioned above, nucleus condensation and DNA fragmentation are the two morphological characteristics of cells under apoptosis. These results suggest that the isolated Apogen L contains an activity inducing apoptosis in HL-60 cells. Apogen L also induces apoptosis in MCF-7 (breast cancer) cells. On the other hand, the conditioned medium fails to induce apoptosis in normal human lung fibroblast (CCD 39 Lu cells).

EXAMPLES

A. Methods

1. Preparation of Condition Media.

A. Preparation of XC Condition Medium for Isolation of Apogen P-1.

Apogen P-1 was isolated from the conditioned medium of a cell line called XC, which was derived from a rat tumor (ATCC CCL 165). XC cells were first seeded in a roller bottle (Polystyrene, area surface=850 Cm2, Corning) in Dulbecco's Modification of Eagle's Medium (DMEM) containing $CO_2$, 10% fetal bovine serum (FBS), nonessential amino acids, penicillin and streptomycin for 3 days. XC cells were then washed with PBS (3×100 ml) to remove serum and then grown in 100 ml of DMEM containing no FBS (with $CO_2$, nonessential amino acids, penicillin and streptomycin) for 4 days. The conditioned medium was collected and clarified by centrifugation.

B. Preparation of C3H 10T1/2 Condition Medium for Isolation of Apogen P-2.

Apogen P-2 was isolated from the conditioned medium of a cell line called C3H10T1/2, which was derived from a mouse embryo and was purchased from American Type Culture Collection (ATCC CCL 226). C3H10T1/2 cells were first seeded in a roller bottle (Polystyrene, area surface=850 Cm2, Corning) in alpha Modification of Eagle's Medium (alpha-MEM) containing $CO_2$, 10% Fetal bovine serum (FBS), penicillin and streptomycin for 3 days. C3H10T1/2 cells were then washed with PBS (3×100 ml) to remove serum and then grown in 100 ml of alpha MEM containing no FBS (with $CO_2$, penicillin and streptomycin) for 4 days. The conditioned medium was collected and clarified by centrifugation.

C. Preparation of XC Condition Medium for Isolation of Apogen L.

Apogen L was isolated from the conditioned medium of a cell line called XC, which was derived from rat tumor (ATCC CCL 165). XC cells were first seeded in a roller bottle (Polystyrene, area surface=850 Cm2, Corning) in Dulbecco's Modification of Eagle's Medium (DMEM) containing penicillin, streptomycin, $CO_2$, non-essential amino acids and 10% Fetal bovine serum (FBS) for 4 days. The conditioned medium was collected and clarified by centrifugation.

2. Assays (a) Cell Death (Apoptosis) Assay

Prostate cancer cell line LNCAP was routinely used for the isolation of Apogen P-1 and Apogen P-2, whereas leukemia cell line HL-60 was used for the isolation of Apogen L. The methods of assays were as follows: LNCAP or HL-60 (1,000 cells) was seeded in 10 microliters RPMI containing 15% or 20% Fetal bovine serum, penicillin and streptomycin at 37 degrees, 5% $CO_2$ in Microtray plates (25 µl wells, Robbins Scientific Corp.). The tested sample (10 µl) was added 3-4 hours after cells were seeded. After incubation of the tested sample with cells for 15 hours, two microliters of Hoechst dye (0.03 ng/ml in PBS) was added. Two hours later, cells that were stained with Hoechst dye were examined under fluorescence microscope. The nuclei of apoptotic cells showed DNA condensation and fragmentation, which were easily identified by Hoechst dye staining. The percentage of apoptotic cells was calculated by the following equation:

$$\% \text{ Apoptotic cells} = \frac{\text{Number of cells with DNA condensation and fragmentation}}{\text{Total cell number}}$$

(b) Cell Repelling Assay

There are two reasons that Hep G2 cells were chosen for the study of cell repelling activity. First, Hep G2 cells are not sensitive to Apogen P-1 in inducing apoptosis. Second, the cell size of Hep G2 cell is about 3-4 times as big as the pore size of the membrane on the Transwell Insert, which is a good cell size for cell migration/invasion study. A tissue culture device called Transwell Insert purchased from Costar (Cambridge, Mass.) was used to discover the chemorepellent activity of Apogen P-1b. This device, which has been widely used for the studies of cell migration/invasion, contains an upper chamber and a lower chamber. Between these two chambers is a polyester microporous membrane with 3.0 μm pore size, which allows cells to migrate through the membrane. Tested cells were grown on the upper chamber, and the tested compound was placed in the lower chamber. If this tested compound is a chemoattractant, more cells will migrate through membrane than the control sample. In our experiments, Hep G2 (100,000 cells) cells, which have a cell size 3-4 times as big as the membrane pore size were grown in the upper chamber (Minimum Essential Medium Eagle containing 10% FBS, PS and nonessential amino acid, 0.1 ml) for 2 hours, and then the partially purified Apogen-1b (30 μl) isolated by ammonium sulfate precipitation and Q2 HPLC chromatography as described above was placed in the lower chamber which contained 0.6 ml of the same growth medium for Hep G2 cells. After 15 hours, cells that had migrated through the membrane were collected by treating the membrane with 0.2 ml of trypsin solution for 30 min. Cells in ten microliters of the trypsin solution were counted in a hemacytometer.

3. Protein Isolation

A. Isolation of Apogen P-1

Step 1: Ammonium Sulfate Precipitation

Apogen P-1 was precipitated by 80% saturated of ammonium sulfate by adding 561 g of ammonium sulfate per liter of XC conditioned medium. The pellet was collected by centrifugation, and the proteins were dissolved in 10 mM Tris-HCl (pH 7.4). After removal of ammonium sulfate by dialysis, the dissolved proteins were separated by a Q2 HPLC column.

Step 2: Q2 HPLC Chromatography

The dissolved proteins isolated by ammonium sulfate precipitation were concentrated and loaded onto a Q2 column (Bio Rad) which was further developed by a linear gradient constructed by buffer A (10 mM Tris-HCl, pH 7.4) and buffer B (10 mM Tris-HCl, pH 7.4, 0.55 M NaCl) using BioRad's BioLogic HPLC system. The linear gradient was constructed by increasing buffer B from 0% to 100% in buffer A within 10 min (20 milliliter elution volume) and thereafter the column was eluted with 100% buffer B for 5 min. The Apogen P-1 activity was assayed by the induction of apoptosis in LNCAP cells. Three activity peaks were found across the chromatogram profile. Fractions 5 to 7 caused 70% cell death; fractions 8-10 caused 65% cell death; and fractions 11-14 caused 90% cell death in 18 hr. We collected fractions 5-7 and named it Apogen P-1a; fractions 8-10 was named Apogen P-1b; and fractions 11-14 was named Apogen P-1c. These three Apogen P-1's were further purified by a reverse phase column.

Step 3: Reverse Phase Chromatography.

Apogen P-1a, Apogen P-1b and Apogen P-1c were separately concentrated to 1.5 ml. One ml of methanol containing 0.05% Trifluoracetic acid was added. In each sample, a large amount of protein was precipitated by this treatment. Whereas, the apoptosis inducing activity remained in the supernatant. The supernatant was then applied to a reverse phase RP-4 column (Micra Scientific Inc) and developed by a linear gradient constructed by solution A (H2O, 0.05% TFA) and solution B Methanol, 0.05% TFA). The linear gradient was constructed by increasing solution B from 0% to 100% in solution A within 10 min. (20 milliliter elution volume) and thereafter the column was eluted with 100% solution B for 5 min.

Step 4: Preparative Electrophoresis

Apogen 1c isolated by anion exchange chromatography was purified by both Reverse Phase Chromatography (step 3) and Preparative Electrophoresis by a MiniPrep Gel electrophoresis (Bio-Rad). In the reverse phase chromatogram of Apogen P-1a, fractions 12-13 had activity inducing 80% cell death in LNCAP cells at 10 hr.

In the reverse phase chromatogram of Apogen P-1b, fractions 14 and 15 had activity inducing 45% cell death in LNCAP cells at 18 hr.

In the reverse phase chromatogram of Apogen P-1c, fraction No. 5 had activity inducing 52% cell death in LNCAP cells at 18 hr.

The purity of the isolated Apogen P-1a, Apogen P-1b and Apogen P-1c were checked with SDS-polyacrylamide gel electrophoresis stained with silver staining.

(1) Apogen P-1a: A protein band with molecular weight of 70 KD was obtained. This result suggests the successful purification of Apogen P-1a, which has a molecular weight of 70 KD on SDS-PAGE.

(2) Apogen P-1b: A single faint protein band with molecular weight of 55 KD was obtained. This result suggests the successful purification of Apogen P-1b, which has a molecular weight of 55 KD on SDS-PAGE.

(3) Apogen P-1c: The purification of Apogen 1c by Reverse Phase chromatography lead to the Isolation of a 70 KD protein, whereas the purification of Apogen 1c by preparative electrophoresis leads to the purification of a 57 KD protein. A major protein band with molecular weight of 70 KD was obtained by Reverse Phase chromatography. A 57 KD protein, on the other hand, was isolated by preparative electrophoresis.

B. Isolation of Apogen P-2

The Apogen P-2 present in C3H10T1/2 conditioned medium was isolated by the following steps:

Step 1: Ammonium Sulfate Precipitation.

Apogen P-2 was precipitated by ammonium sulfate (80% saturated) by adding 561 g of ammonium sulfate per liter of conditioned medium. The pellet was collected by centrifugation, and the proteins were dissolved in 10 mM Tris-HCl (pH 7.4).

Step 2: Hydroxylapatite Treatment.

After removal of ammonium sulfate by dialysis in 10 mM Tris-HCl (pH 7.5), the dissolved proteins were incubated with hydroxylapatite gel (Bio-Gel HTP gel, Bio-Rad) for 1 hr. After removing HTP gel by centrifugation, the activity inducing apoptosis in LNCAP cells was found to be present in the supernatant, which was then further treated with Heparin agarose gel.

Step 3: Heparin Agarose Treatment.

The supernatant from step 2 was further incubated with Heparin agarose (Sigma) for 1 hr. After removing HTP gel by centrifugation, the activity inducing apoptosis in LNCAP cells was found to be present in the supernatant.

Step 4: Reverse Phase Chromatography.

Apogen P-2 present in the supernatant of Heparin agarose in step 3 was further purified by reverse phase chromatography. Apogen P-2 was concentrated to 1 ml. One milliliter of methanol containing 0.05% trifluoacetic acid was added. Large amounts of proteins were precipitated by this treatment. Whereas, the apoptosis inducing activity (P-2) remained in the supernatant. The supernatant was then applied to a reverse phase RP-4 column (Micra Scientific Inc.) and developed by a linear gradient constructed by solution A (H2O, 0.05% TFA) and solution B Methanol (0.05% TFA). The linear gradient was constructed by increasing solution B from 0% to 100% in solution A within 10 min (20 milliliter elution volume) and thereafter the column was eluted with 100% solution B for 5 min. In the reverse phase chromatogram of Apogen P-2, fractions 12-14 have activity inducing 80% cell death in LNCAP cells at 12 hr. The purity of the isolated Apogen P-2 was checked with SDS-polyacrylamide gel electrophoresis stained with silver staining. A single protein band with molecular weight of 65 Kd was obtained.

C. Isolation of Apogen L

The Apogen L present in the conditioned medium was isolated by the following steps:

Step 1: DE52 Absorption

The conditioned medium was incubated with the anion exchanger, DE 52 (Diethylaminoethyl cellulose, Whatman) for 1 hr. The incubation mixture was centrifuged, and DE 52, which binds Apogen L, was collected and washed with 10 mM Tris-HCl (pH 7.5) containing 0.15 M NaCl. Apogen L was then eluted from DE 52 cellulose by 10 mM Tris-HCl (pH 7.5) containing 0.5 M NaCl.

Step 2: Heparin Agarose Absorption

Apogen L isolated as described in step 1 was further absorbed by Heparin agarose (Sigma) by incubating Apogen L with Heparin agarose for 1 hr. Heparin agarose was collected by centrifugation and was washed with 10 mM Tris-HCl (pH 7.5). Apogen L absorbed in Heparin agarose was then eluted by 2 M NaCl.

Step 3: Q2 HPLC Chromatography

Apogen L isolated as described above was concentrated and loaded onto a Q2 column (Bio Rad) which was further developed by a linear gradient constructed by buffer A (10 mM Tris-HCl, pH 7.4) and buffer B (10 mM 22 Tris-HCl, pH 7.4, 0.5 M NaCl) using Bio-Rad's BioLogic HPLC system. The linear gradient was constructed by increasing buffer B from 0% to 100% in buffer A in 10 min. The purity of the isolated Apogen L was checked with SDS-polyacrylamide gel electrophoresis stained with silver staining. A single protein band having activity with a molecular weight of approximately 55 Kd was obtained.

4. Isolation of Bovine Fetuin as a Component of Protein P-2 and the Apoptotic Effect Thereof in Tumor Cell Lines.

The observation that Apogen P-1a, P-1b, P-1c, P-2 and L were isolated from embryonic cell lines led us to speculate that newborn or embryonic tissue may secrete "Apogen," which may selectively induce apoptosis in tumor cell lines. Based on this speculation, our attention turned towards a protein named "Fetuin" for the following reasons: (1) Fetuin is mainly a fetal protein, in the sense that the highest concentrations are found in serum and body fluids of embryos and fetuses. For example, the concentration of fetuin in bovine serum drastically decreases, probably within a few days after birth, to 1-2% of the fetal level. (Yang, et al., Biochim. Biophy. Acta. 1130, 149-156 1992). (2) A histochemical study has shown that fetuin may control tissue remodelling and physiological cell death during embryonic development. (Von Bulow, et al., Histochemistry 99:13-22, 1993). These features of fetuin suggest the possibility that fetuin may contain activity inducing cell death (apoptosis).

Additionally, a protein with an amino acid sequence identical to Fetuin was isolated from the preparation of Apogen P-2. Thus, the composition of Apogen P-2 consists at least in part of fetuin. Therefore fetuin was prepared and tested for apoptotic activity. Interestingly, it was found that only bovine fetuin prepared by a special method was able to induce apoptosis in tumor cell lines. The commercial fetuin that is prepared by ammonium sulfate precipitation and EDTA treatment was found to contain a very low activity in inducing apoptosis in tumor cells.

4A. Preparation of Bovine Fetuin.

Bovine fetuin was prepared by the modified Spiro method (Spiro R. G., Journal of Biological Chemistry 235, 10: 2860, 1960) according to the following steps:

1. One hundred milliliters of Fetal Bovine Serum (FBS).
2. Add two hundred milliliters of 0.05 M Zinc Acetate containing 30% (V/V) ethanol, adjust to pH 6.4 by 1M NH4OH—NH4Cl, let stand 15 hours at −5° C.
3. Collect the supernatant by centrifugation, add 1.0 M Barium Acetate and 95% ethanol to give 0.03 M Barium Acetate, 25% ethanol. Let stand 2 hours at −5° C.
4. Collect the supernatant by centrifugation, add 95% ethanol to give 40% ethanol. Let stand 15 hours at −10° C.
5. Collect the precipitate. Dissolve the pellet by phosphate buffer saline.

The purified fetuin showed a single protein band with apparent molecular weight of 63 Kd on SDS-PAGE.

4B. Induction of Apoptosis in Tumor Cell Lines Using Bovine Fetuin.

Fetuin purified from fetal bovine serum by the procedure described above was dissolved in phosphate buffer saline (PBS). The free Zinc Acetate and Barium Acetate were removed by repetitive concentration. Fetuin was tested in LNCaP and HL-60 cells. LNCaP or HL-60 (1,000 cells) was seeded 10 microliters RPMI containing 15% or 20% Fetal bovine serum, penicillin and streptomycin at 37 degree, 5% CO2 in microtray plates (25 µl wells, Robbins Scientific Corp.). Fetuin (in 10 µl PBS) at concentration of 100 ng/ml was added 3-4 hours after the cells were seeded. After incubation of the tested sample with the cells for 15 hours, two microliters of Hoechst dye (0.03 ng/ml in PBS) was added. Two hours later, cells that were stained with Hoechst dye were examined under fluorescence microscope. The nuclei of apoptotic cells showed DNA condensation and fragmentation, which were easily identified by Hoechst dye staining. The percentage of apoptotic cells was calculated by the following equation:

$$\% \text{ Apoptotic cells} = \frac{\text{Number of cells with DNA condensation and fragmentation}}{\text{Total cell number}}$$

The nuclei of the LNCaP cells that were incubated with control sample (PBS) were normal and healthy. However, the nuclei of the LNCaP cells that were incubated with fetuin (100 ng/ml in PBS) showed the characteristics of apoptosis. First, the cells in the presence of fetuin showed condensation of the nucleus as demonstrated by the more intense fluorescent light compared with the control nucleus. Second, the nucleus condensation was accompanied by the fragmentation of DNA as demonstrated by breakage of the nucleus. As condensation of the nucleus and DNA fragmentation are the two morphological characteristics of cells under apoptosis, these results suggest that fetuin contains an activity inducing apoptosis in LNCaP cells. Furthermore, the nuclei of the HL-60 cells that were incubated with control buffer (PBS) were normal and healthy. However, the nuclei of the HL-60 cells that were incubated with fetuin showed the characteristics of apoptosis. Fetuin caused condensation of the nucleus as demonstrated by the more intense fluorescent light compared with the control nucleus. Second, the nucleus condensation was accompanied by the fragmentation of DNA as demonstrated by breakage of the nucleus. As mentioned above, the nucleus condensation and DNA fragmentation are the two morphological characteristics of cells under apoptosis. Accordingly, these results suggest that fetuin contains an activity inducing apoptosis in HL-60 cells.

4C. Bovine Fetuin Selectively Induces Apoptosis in Cancer Cells Without Having an Effect on Normal Cell Lines.

The effect of fetuin on the induction of apoptosis was compared in various cell lines. At a concentration of 50 µg/ml, fetuin prepared as described above strongly induced apoptosis in tumor cell lines such as: LNCaP (prostate cancer), PC-3 (prostate cancer), HL-60 (leukemia), MCF-7 (breast cancer), Colo 205 (colon cancer), Calu-1 (lung cancer). Normal lung fibroblast (CCD 39 Lu), on the other hand, is not affected by fetuin.

Fetuin at 25 µg/ml highly induced apoptosis in LNCaP, HL-60 cells, and MCF-7 cells while it was found to be inactive in inducing apoptosis in CCD 39 Lu cells. Fetuin (25 µg/ml) prepared as described above was incubated with CCD 39 Lu cells grown in MEM in a microtray plate for 15 hours. The CCD 39 Lu cells remained morphologically unchanged in the presence of fetuin.

4D. Only Fetuin Prepared by the Method Described Above is Able to Induce Apoptosis in Tumor Cell Lines.

Fetuin purchased from Sigma has a very low activity in inducing apoptosis in LNCaP cells. For the fetuin purchased from Sigma, apoptosis inducing activity was observed only at a very high concentration (>250 µg/ml) and at long incubation time (2 days). However, fetuin (25 µg/ml) prepared by the method described in Section 4A above induced apoptosis in LNCaP cells by up to 90% in 4 hours. It was initially estimated that the apoptotic activity of fetuin prepared as described in Section 4A above is more than fifty thousand folds higher than that of fetuin prepared by other methods.

In the years of research following the original findings, it has been determined that fetuin from Sigma induces apoptosis at a very high concentration and at a long incubation time. It is conservatively estimated that the fetuin as prepared in Section 4A has more than one hundred times greater apoptotic activity than fetuin prepared by other methods. While this is not as dramatic as the 50,000 times increase as originally reported, it still represents a significant apoptotic advantage over previously available fetuin in terms of incubation time and $LD_{50}$ values (dosage for the induction of 50% cell death).

Sigma's fetuin is prepared by methods which include ammonium sulfate precipitation and EDTA treatment. Both of these treatments may cause deprivation of the Zinc ion from the protein, which may cause the irreversible loss of the protein's apoptotic activity.

4E. Effect of Fetal Fetuin on Leukemia Cells In Vivo.

The previous data demonstrate that fetuin induces apoptosis in cancer cells in vitro. The data provided below shows that the in vivo testing of fetuin in mice having leukemia was successful. The results show that fetuin has an anti-leukemia effect in mice. FIG. 1 shows the increase in survival of leukemia-bearing mice treated with fetal fetuin.

Method

Forty DBA/2 female mice (17-20 grams; Simonsen Laboratories, Inc., Gilroy, Calif.) kept on a standard diet and water ad libitum were inoculated with tumor cell line P388D1 (ATCC cell line number CCL46). The mice were randomly segregated into groups of ten (10). Zinc-charged fetal fetuin (10 mg/ml) were intraperitoneally injected into group I at 0.002 ml/mouse, group II at 0.02 ml/mouse and group III at 0.2 ml/mouse. Group IV was the control group, which was injected with 0.5 ml of saline solution. The injections were continued for 10 days. Mortalities were recorded for 60 days. The results were expressed as the percentage increase in life span (ILS):

$$ILS = \frac{100 \times \text{Median Life Span Treated} - \text{Median Life Span Controlled}}{\text{Life Span Controlled}}$$

FIG. 1 shows that while 100% of the untreated leukemia-bearing mice were dead after 24 days, 80% of the mice treated with a high dose of fetuin, namely 100 mg/Kg of fetal fetuin, survived more than 58 days. This in vivo experiment demonstrates that mice bearing leukemia that are treated with fetal fetuin have an increased life span of 141%.

4F. Method of Preparing Supercharged Zinc Fetuin:

The method of preparing fetuin with zinc was refined and improved. As stated above, fetuin prepared by the method as described in Section 4A above is able to induce apoptosis in tumor cell lines. However, commercial fetuin such as that from Sigma is found to have a very low activity in inducing apoptosis in tumor cells and in inducing apoptosis in LNCaP cells. For fetuin from Sigma, apoptosis inducing activity was observed only at a very high concentration (>250 µg/ml) and at a long incubation time (2 days), whereas fetuin (25 µg/ml) as prepared in Section 4A above induced apoptosis in LNCaP cells by up to 90% in 4 hours. It was initially estimated that the apoptotic activity of fetuin as prepared as described in Section 4A is more than fifty thousand times higher than that fetuin prepared by other methods. The radically different results suggest a fundamental difference in the chemical composition of commercially available fetuin and the fetuin prepared in accordance with the procedure in Section 4A.

In the years of research following the original findings, it was observed that fetuin from Sigma induced apoptosis at a very high concentration (>>5 mM) and at a long incubation time (2 days), whereas fetuin (approximately 50 µM) as prepared in Section 4A above induced apoptosis in LNCaP cells by up to 90% in 4 hours. It is conservatively estimated that the fetuin as prepared in Section 4A has more than one hundred times greater apoptotic activity than fetuin prepared by other methods. While this is not as dramatic as the 50,000 times increase as originally reported, it still represents a significant apoptotic advantage over previously available fetuin in terms of incubation time and $LD_{50}$ values (dosage for the induction of 50% cell death).

After looking at the methods of preparing commercially available fetuin, it was found that ammonium sulfate precipitation and EDTA treatment was used in preparing fetuin. It was speculated that this ammonium sulfate precipitation and EDTA treatment might cause deprivation of the ions from the protein causing irreversible loss of the protein's apoptotic activity. However, it was not known whether it was the loss of zinc alone, or in combination with the loss of another ion(s), that caused the decreased apoptotic activity in commercially available fetuin. While it was determined that Fetuin-Ca is inactive in inducing apoptosis (data not shown), and barium occurs in only trace amounts, to determine which ion, or combination of ions, were most effective in increasing the apoptotic ability of fetuin, fetuin as prepared in Section 4A above was treated with a chelating agent, such as EDTA, to strip all the inorganic ions, including zinc, calcium, and barium from the protein. After removing these inorganic ions, the "naked" fetuin was treated or incubated with 0.5 M Zinc Acetate to reload or to bind the fetuin with zinc only. The results of this refinement process are shown in FIGS. 2-3. $LD_{50}$ (dosage for the induction of 50% cell death) concentrations on LNCaP cells incubated for 6 hours reveal that the improved preparation of Fetuin-Zn or "supercharged zinc fetuin" enhances fetuin's ability to induce apoptosis in cancer cells by three to four times as compared with the original fetuin bound with zinc as prepared in Part 4A. It is hypothesized that the fetuin previously bound up with calcium and barium created an inactive form of the protein. By stripping out all ions and replacing them with zinc, inactive fetuin molecules were converted to active form, thereby explaining the dramatic increase in apoptotic activity. Such supercharged zinc fetuin is a valuable step forward in the fight against cancer.

In one preferred embodiment of this preparation process:

1. Incubation Mixture: 700 μg of fetuin (0.2 ml; as prepared by the method as described above in Section 4A) was incubated with 0.5 ml of 50 mM EDTA for approximately one (1) hour.

2. Concentration: Add 1.5 ml of saline solution to this incubation mixture and concentrate to near dryness using a molecular sieve and centrifugal force. Repeat this procedure four (4) times, so that most of the inorganic ions and EDTA are removed. This "naked" fetuin will be retained on the top of the filter (molecular sieve).

3. Incubate the "naked" fetuin (0.2 ml) with 0.5 ml of 0.5 M Zinc Acetate for approximately three (3) hours.

4. Remove the free Zinc Acetate using the combination of the saline solution, the molecular sieve, and centrifugal force as described in Step 2 above.

5. A Specific Peptide Fragment From Fetuin-Zinc That Causes Apoptosis In Cancer Cells.

a. Preparation of Fetuin Fragment:

As described above in Section 4F (Method of Preparing Supercharged Zinc Fetuin), supercharged zinc fetuin was prepared by pre-treatment of fetal bovine fetuin with a chelating agent (EDTA) to remove the inorganic ions, including zinc, calcium, and barium ions, from the fetuin. The resulting stripped fetuin was incubated with 0.5 M Zinc Acetate in order to "supercharge" or load the fetuin with zinc.

Three hundred (300) micrograms of supercharged zinc fetuin was dissolved in a 50 μl saline solution and then dried in a tube under a vacuum. It is hypothesized that this drying step breaks apart the supercharged zinc fetuin into peptide fragments.

Figure 5:
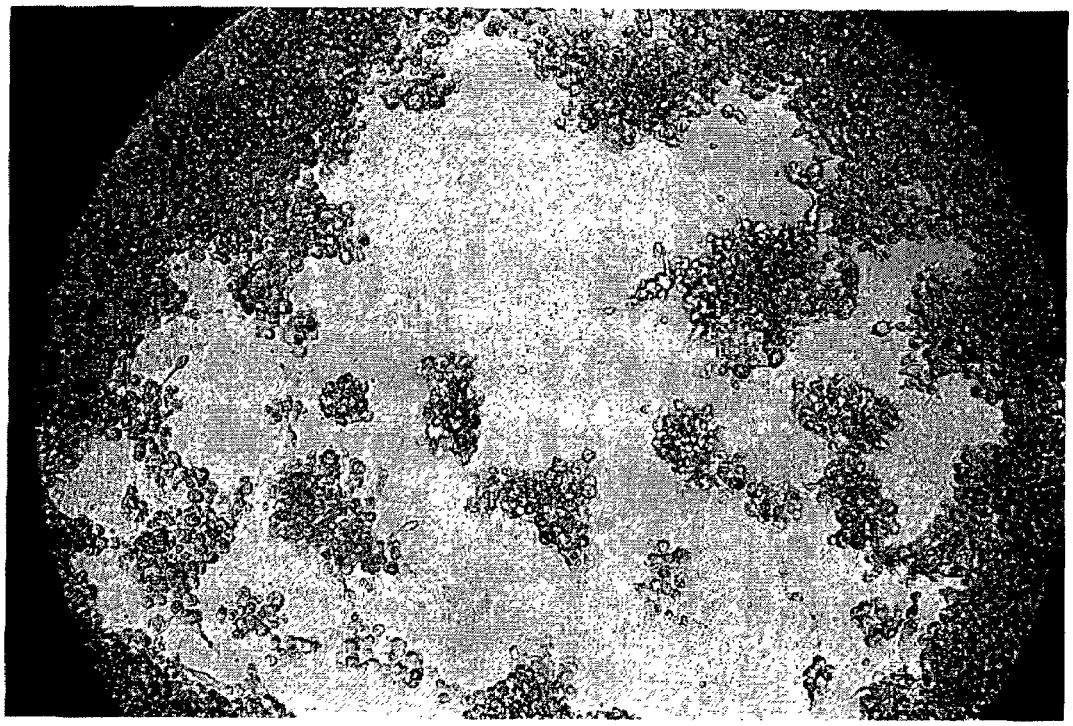
FIG. 5 shows a slide of LNCaP cells incubated with filtrate containing SEQ ID NO: 1 for six (6) hours.
Figure 6:
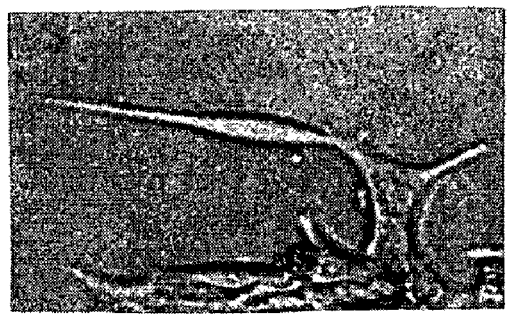
FIG. 6 shows an additional slide of LNCaP (prostate cancer) cells without treatment of filtrate containing SEQ ID NO: 1.
Figure 7:
FIG. 7 shows a slide of LNCaP cells incubated with filtrate containing SEQ ID NO: 1 and which expressed membrane blebbing, which is an indicator of cells undergoing apoptosis.

The dried fragments (of supercharged zinc fetuin) were reconstituted in 50 μl water. This fragment solution was passed through a molecular sieve membrane having a molecular weight cut-off of 10,000 daltons. The resulting filtrate of fragments was collected and tested on cells in an apoptosis assay. As shown in FIG. 5, when LNCaP cells are incubated with the supercharged zinc fetuin fragment filtrate for six (6) hours, the LNCaP cells detach and die. Compared with the control (LNCaP with no filtrate) as shown in FIG. 4, FIG. 5 shows that incubation of the prostate cancer cells with the supercharged zinc fetuin fragment filtrate causes apoptosis of the cancer cells. FIG. 7 shows that the supercharged zinc fetuin fragment filtrate treated LNCaP cells also exhibit membrane "blebbing," which is a characteristic typical of cells undergoing apoptosis. FIG. 6, which shows LNCaP cells without the supercharged zinc fetuin fragment filtrate, lacks this membrane "blebbing" and characteristic of apoptosis.

b. The Apoptosis Inducing Activity is Protease Sensitive.

Additionally, the apoptosis-inducing activity of the supercharged zinc fetuin fragment filtrate was found to be protease sensitive. Incubation of the supercharged zinc fetuin fragment filtrate with proteinase K completely removed the apoptosis-inducing activity. Proteinase K is an enzyme that cleaves peptide bonds.

After preparing "supercharged" zinc fetuin as stated in Section 4F above, the resulting composition was dried in a tube and under a vacuum. This dried supercharged zinc fetuin was reconstituted in 50 μl of water. This solution was filtered through a molecular sieve membrane (Centricon 10 tube with a molecular weight cut-off: 10,000 daltons). The filtrate was collected and treated with 5 μl (1 unit/μl) proteinase K for three (3) hours at 37° C. After treatment with proteinase K, the treated filtrate was filtered through a molecular sieve membrane (Centricon 10 tube) in order to remove the proteinase K. The proteinase K was retained by the membrane, and the treated filtrate passed through the membrane.

To test the effect of a protease on the apoptotic activity of the filtrate, the filtrate treated with proteinase K was tested on cancer cells. These results were compared to the filtrate that was not treated with proteinase K.

The effect of proteinase K on the apoptotic ability of the Fetuin-Zinc fragments is summarized in FIG. 8. Experiments 1 and 2 were conducted with one set of supercharged zinc fetuin fragment filtrate, and Experiment 3 was conducted with another set of supercharged zinc fetuin fragment filtrate. FIG. 8 shows that incubation with a protease seems to inactivate the apoptotic effect of the zinc charged fetuin fragment. Because a protease, such as proteinase K, cleaves peptide bonds, the test results of FIG. 8 strongly suggest that a peptide or a protein of fetuin is responsible for the induction of apoptosis in cancer cells.

c. The Filtrate Contains Two Major Peptides Derived from Fetuin.

The dried and reconstituted filtrate was found to contain peptide fragments. The amino acid sequence analysis revealed two major peptide fragments in the filtrate:

(1) H-T-F-S-G-V-A-S-V-E (amino acid no. 300-309; His Thr Phe Ser Gly Val Ala Ser Val Glu; SEQ ID NO: 1) and (2) S-A-S-G-E-A-F-H (amino acid no. 310-317; Ser Ala Ser Gly Glu Ala Phe His; SEQ ID NO: 2) of fetuin.

Figure 9:
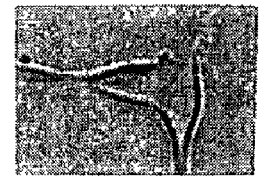
FIG. 9 shows a slide of LNCaP cells without filtrate containing SEQ ID NO: 1.
Figure 10:
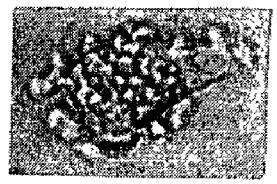
FIG. 10 shows a slide of LNCaP cells, which were incubated with filtrate containing SEQ ID NO: 1 for three (3) hours and expressed membrane "blebbing," which is an indicator of cells undergoing apoptosis.

To identify which of these peptide fragments was responsible for the apoptosis-inducing activity, the two fragments (H-T-F-S-G-V-A-S-V-E, amino acid no. 300-309, SEQ ID NO: 1 and S-A-S-G-E-A-F-H amino acid no. 310-317, SEQ ID NO: 2) of the full-length fetuin molecule) were chemically synthesized. Upon in vitro testing of these chemically synthesized peptide fragments, SEQ ID NO: 1 was shown to have the greater apoptotic activity. LNCaP (prostate cancer cells) were incubated with SEQ ID NO: 1. In FIG. 10, chemically synthesized SEQ ID NO: 1 caused membrane "blebbing" in LNCaP cells after three (3) hours of incubation. Incubation of SEQ ID NO: 2 with LNCaP cells did not show any apoptotic activity or membrane "blebbing." FIG. 9 shows the control of LNCaP cells without SEQ ID NO: 1. These results suggest that the peptide fragment that induced apoptosis and that was present in the filtrate corresponds to amino acid no. 300-309, SEQ ID NO: 1 of full-length fetuin.

6. Characterization of SEQ ID NO: 1.

a. SEQ ID NO: 1 Selectively Induced Apoptosis in Cancer Cells but not in Normal Cells.

Previously, it was found that fetuin and supercharged zinc fetuin induced apoptosis in various cancer cells without affecting certain normal cells. To test whether SEQ ID NO: 1 derived from fetuin retains this selectivity in inducing apoptosis in cancer cells only while not affecting normal cells, various concentrations of SEQ ID NO: 1 were tested on HT-29 (colon cancer), CCD-18 Co (normal colon), and LNCaP (prostate cancer) cells. As shown in FIG. 11, SEQ ID NO: 1 induced apoptosis in HT-29 and LNCaP cells without affecting CCD-18 Co cells. These results suggest that the fragment was similar to fetuin and supercharged zinc fetuin in selectively inducing apoptosis in cancer cells while not affecting normal cells.

b. SEQ ID NO: 1 Rapidly Induced Apoptosis in HT-29 (Colon Cancer) Cells.

Figure 12:
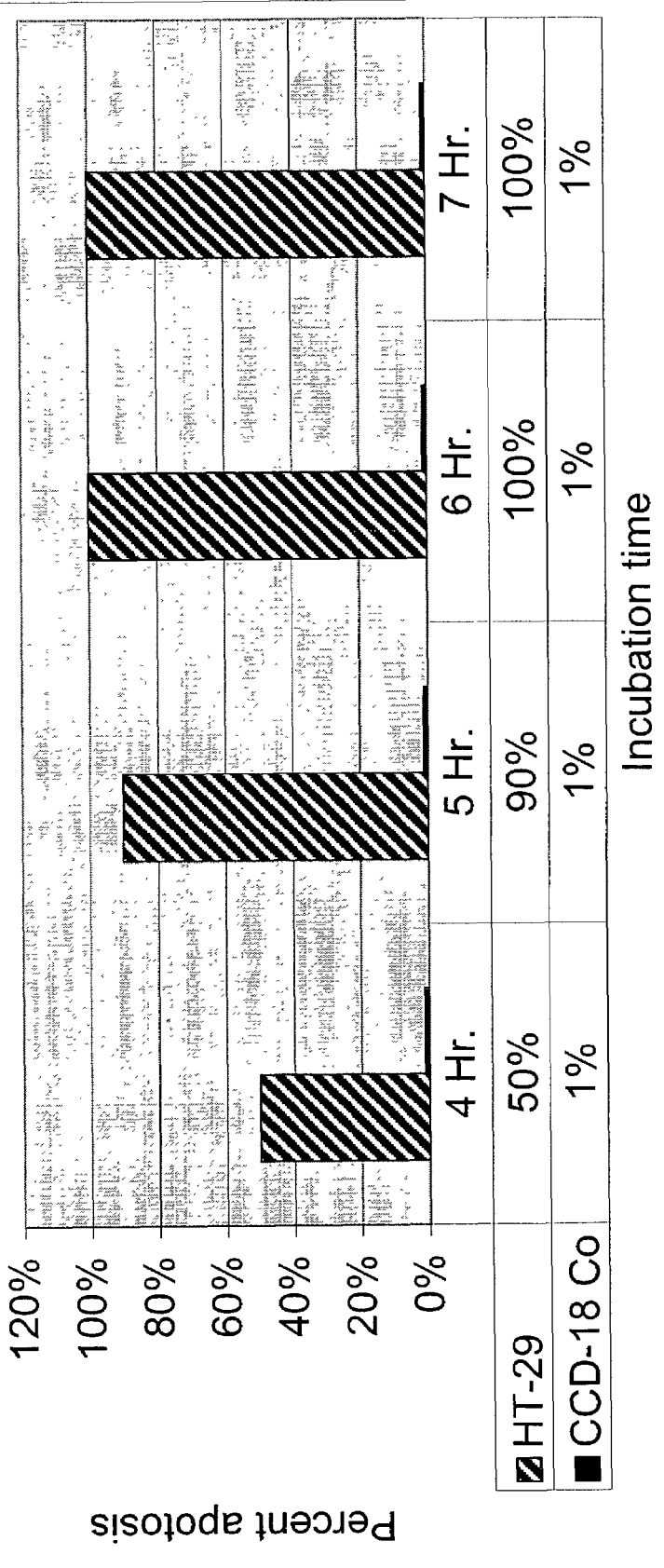
FIG. 12 is a graph of the time of incubation of SEQ ID NO: 1 filtrate versus percent apoptosis in HT-29 and CCD-18 Co cells.

FIG. 12 shows the effect of time on the induction of apoptosis by SEQ ID NO: 1. At four (4) hours, SEQ ID NO: 1 at a concentration of 0.4 µM induced apoptosis in 52% of the HT-29 colon cancer cells. At six (6) hours, almost all of the HT-29 cells were induced to apoptosis. Even the slightest increase in incubation time (from 4 to 6 hours), dramatically increased the apoptotic affect of SEQ ID NO: 1.

c. The Peptide Fragment Derived from Fetuin is More Potent than Full Length Fetuin or Supercharged Zinc Fetuin in Inducing Apoptosis.

Previously, the $LD_{50}$ (dosage for the induction of 50% cell death) at 6 hours for full-length supercharged zinc fetuin in LNCaP cells was determined to be 3-10 µM. Preliminary results for the $LD_{50}$ at 6 hours for the supercharged zinc fetuin filtrate were determined to be 0.3-0.4 µM. Therefore, a much smaller amount of fragment was required to induce apoptosis in cancer cells than is required with full-length supercharged zinc fetuin. Further, SEQ ID NO: 1 is more potent in inducing apoptosis than its parent molecule (FIG. 13).

Taking into consideration the previous estimates:
(1) Fetuin as prepared in Section 4A above is approximately 100 times more powerful than fetuin prepared from other methods;
(2) "Supercharged" Zinc Fetuin is approximately three to four times more powerful than the fetuin as prepared in Section 4A (see FIGS. 2-3); and
(3) SEQ ID NO: 1 is approximately eight to ten times more powerful than "Supercharged" Zinc Fetuin (see FIG. 13), it is estimated that SEQ ID NO: 1 is approximately several thousand times more powerful than fetuin prepared from other methods.

The most current results reveal a minor variation from the original results depending on whether the peptide sequence is chemically synthesized, versus whether it is a fragment derived from supercharged zinc fetuin. SEQ ID NO: 1 derived from supercharged zinc fetuin has an $LD_{50}$ at 6 hours of approximately 0.7 µM as compared to SEQ ID NO: 1 that is chemically synthesized which has an $LD_{50}$ at 6 hours of approximately 2.5 µM.

7. Other Sequences of Fetuin from Other Sources.

In addition, peptide sequences were determined from other animal sera, including pig, sheep and mice. K. M. Dziegielewska, et. al., *Fetuin,* 16-17, (R. G. Landes Co. 1995). These peptide sequences have a similarity of 60-90% with the fetuin isolated from bovine serum. These similar fetuin peptide sequences also have valuable apoptotic activity. The peptide sequences for SEQ ID NO: 1 for other species are:

```
Human  (H-T-F-M-G-V-V-S-L-G; His Thr Phe Met Gly Val Val Ser Leu Gly; SEQ ID NO:3);

Pig    (H-S-F-S-G-V-A-S-V-E; His Ser Phe Ser Gly Val Ala Ser Val Glu; SEQ ID NO:4);

Sheep  (H-T-F-S-G-V-A-S-V-E; His Thr Phe Ser Gly Val Ala Ser Val Glu; SEQ ID NO:5);

Rat    (H-T-F-S-G-V-A-S-V-E; His Thr Phe Ser Gly Val Ala Ser Val Glu; SEQ ID NO:6); and Mouse  (H-A-F-S-P-V-A-S-V-E; His Ala Phe Ser Pro Val Ala Ser Val Glu; SEQ ID NO:7). Id.
```

The $LD_{50}$ at 6 hours for the chemically synthesized fetuin fragments for SEQ ID NO's: 3, 4 and 7 are 1.0 µM, 0.3 µM and 0.5 µM respectively. The $LD_{50}$ at 6 hours for the chemically synthesized fetuin fragments for SEQ ID NO's: 1, 5 and 6 are 2.5 µM. A summary of these results reflects that fetuin fragments prepared using the methods taught herein have selective apoptotic activity. In addition, active fragments from naturally occurring fetuin that have been modified as suggested herein or fragments chemically synthesized also have selective apoptotic activity.

8a. Recombinant Fetuin

The studies described above demonstrated the apoptotic activity of fetuin and its fragments. It was observed that when the carbohydrate moiety of natural fetuin was removed by certain enzymes, then the apoptotic inducing activity was boosted 2-3 fold. Accordingly, experiments were done to test the apoptotic activity of recombinant fetuin expressed in *E. Coli*. The *E. Coli*-expressed fetuin had apoptotic activity with an $LD_{50}$ at 6 hours of 1 µM. This is about 5 times greater than the apoptotic activity of supercharged zinc fetuin as prepared in Section 4F above.

EXAMPLE

1. Molecular Cloning of the Bovine Fetuin Gene.

Fetal bovine tissue was obtained commercially. mRNA was then isolated (Frederick, M. A. et al., "Short Protocols in Molecular Biology" pp. 5-12, John Wiley & Sons, $2^{nd}$ Ed. 1992). Full length cDNA was reverse transcribed with poly(t) and a plasmid library constructed.

cDNA clones coding for fetuin were screened. The bovine fetuin gene was isolated by traditional methods and subcloned into pBluescript vector. The gene was confirmed by DNA sequencing.

The gene contains one open reading frame encoding 359 amino acid residues, which is homologous with other fetuin genes. The confirmed gene was ligated into vector pCRT7-NT vector and junction was confirmed by both restriction digestion and sequencing (Frederick, M. A. et al., "Short Protocols in Molecular Biology" p. 3, John Wiley & Sons, $2^{nd}$ Ed. 1992). The gene was prepared from confirmed clone in E. coli TOP10 strain.

Over 10 different clones were identified. Protein expression was performed in 1 L and 5 L culture.. Culture was grown at 34 C to OD600 about 0.5-0.6 and then 1 mM IPTG was used to induce expression for 4-5 hours. Precipitated bacterial pellet was used for protein purification. Bacterial pellet was suspended into 20 ml of 1X binding buffer and sonicated on ice. The lysate was run through columns. The eluted protein was dialysed against two changes of 1X PBS at 4C. Further protein purification was carried out by HPLC chrometography.

b. Recombinant Fragment

From E. Coli expressed fetuin, peptide fragments were generated as in Section 5a. Three hundred (300) micrograms of the zinc charged fetuin was dissolved in a 50 μl saline solution and then dried in a tube under a vacuum. The dried fragments were reconstituted in 50 μl water. This fragment solution was passed through a molecular sieve membrane having a molecular weight cut-off of 10,000 daltons.

This peptide filtrate strongly induced apoptosis in LNCaP and HT-29 cells without affecting normal colon cells (CCD 19 Co). The peptide filtrate caused DNA condensation and DNA fragmentation in HT-29 cells. The onset of the induction of cell death by the fragment was very rapid. In as soon as 60 minutes, cell death was observed. The $LD_{50}$ at 6 hours of this recombinant peptide filtrate is 2.5 μM.

9. Supercharged Alpha 2 HS-glycoprotein

The previous studies demonstrated selective apoptotic activity in full length fetuin (as modified in the methods described above) and fragments (whether from modified natural fetuin, chemically synthesized, or recombinantly generated).

The human version of fetuin is called Alpha 2HS-glycoprotein (discovered by J. F. Heremans and K. Schmid in 1961). The amino acid sequence of this protein is about 60% homologous to bovine fetuin. Bovine fetuin and human Alpha 2-HS glycoprotein are truly species homologues and not simple (closely) related proteins. Alpha 2-HS glycoprotein is a glycoprotein found in human serum. The concentration in plasma is higher in fetal (145 mg/100 ml) than in adult (40-60 mg/100 ml). It is known that this protein binds calcium and barium with high affinity. Fetuin levels in human plasma are regulated in the manner of a negative acute phase reactant. As a negative acute-phase reactant, reduced levels of human Alpha 2HS-glycoprotein have been observed in several diseases including Paget's disease of bone (4), various cancers (5-8), and severe malnutrition and infection (9-12).

Since fetuin and its fragments as modified above induced apoptosis, it was hypothesized that the human counterpart of fetuin, Alpha 2-HS glycoprotein, also induced apoptosis. Like fetuin, Alpha 2-HS glycoprotein, modified by the addition of zinc, also selectively induced apoptosis. Specifically, Alpha 2-HS glycoprotein supercharged with zinc was found to induce apoptotic activity in cancer cells at concentrations of 0.75 μM. Since the concentration of Alpha 2-HS glycoprotein in adult human serum is about 0.5 mg/ml (8.3 μM), the 0.75 μM apoptotic threshold is a concentration that can easily be reached by IV administration or other means such as oral administration. It is believed that supercharged zinc Alpha 2-HS glycoprotein and its active fragments may be used to treat cancer along the same lines as immunoglobulins are used for the treatment of certain humans diseases, by first preparing the proteins from human sera and then re-administering them into human patients after active manipulation of the proteins.

This section teaches the selective apoptotic activity of Alpha 2-HS glycoprotein in its naturally occurring (modified by supercharging with zinc), chemically produced, and/or recombinantly produced forms. In addition, this section teaches that the fragments of Alpha 2-HS glycoprotein also have apoptotic activity whether from the modified natural Alpha 2-HS glycoprotein, chemically synthesized or recombinantly generated fragments.

9a. Purification of Alpha2-HS Glycoprotein from Adult Serum

Alpha 2-HS glycoprotein was prepared by a modified Spiro method (Spiro R. G., Journal of Biological Chemistry 235, 10: 2860, 1960) according to the following steps:

1. One hundred milliliters of human serum (from donor or commercial such as CALBIOCHEM)

2. Add two hundred milliliters of 0.05 M Zinc Acetate containing 30% (V/V) ethanol, adjust to pH 6.4 by 1M NH4OH—NH4Cl, let stand 15 hours at −5° C.

3. Collect the supernatant by centrifugation, add 1.0 M Barium Acetate and 95% ethanol to give 0.03 M Barium Acetate, 25% ethanol. Let stand 2 hours at −5° C.

4. Collect the supernatant by centrifugation, add 95% ethanol to give 40% ethanol. Let stand 15 hours at −10° C.

5. Collect the precipitate by centrifugation. Dissolve the pellet by phosphate buffer saline.

The purified fetuin showed a single protein band with apparent molecular weight of 63 Kd on SDS-PAGE.

9b. Method of Preparing Supercharged Zinc Alpha 2-HS Glycoprotein

In one preferred embodiment of this preparation process:

1. Incubation Mixture: 700 μg of Alpha 2-HS glycoprotein (0.2 ml; as prepared by the method as described above in Section 9A) was incubated with 0.5 ml of 50 mM EDTA for approximately one (1) hour.

2. Concentration: Add 1.5 ml of saline solution to this incubation mixture and concentrate to near dryness using a molecular or molecule sieve and centrifugal force. Repeat this procedure four (4) times, so that most of the inorganic ions and EDTA are removed. This "naked" fetuin will be retained on the top of the filter (molecular sieve).

3. Incubate the "naked" fetuin (0.2 ml) with 0.5 ml of 0.5 M Zinc Acetate for approximately three (3) hours.

4. Remove the free Zinc Acetate using the combination of the saline solution, the molecular sieve, and centrifugal force as described in Step 2 above.

Figure 14:
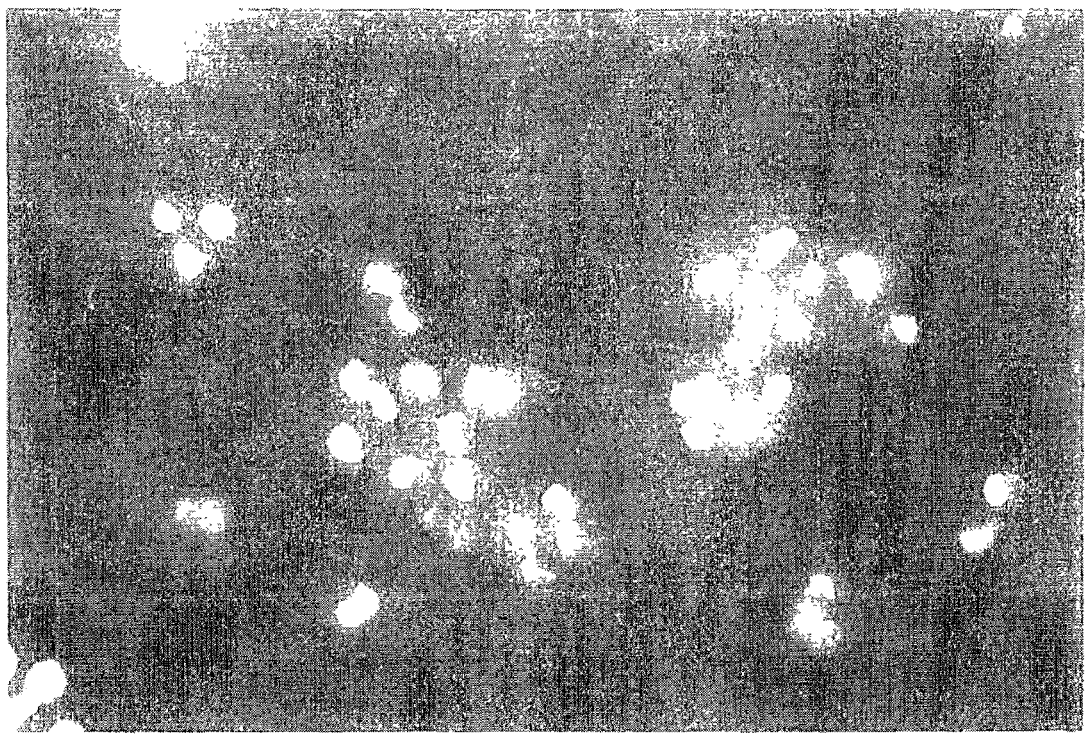
FIG. 14 shows a slide of HT-29 cells incubated with 5 μM Alpha 2-HS Glycoprotein for 4 hours (stained by Hoeschst dye).
Figure 15:
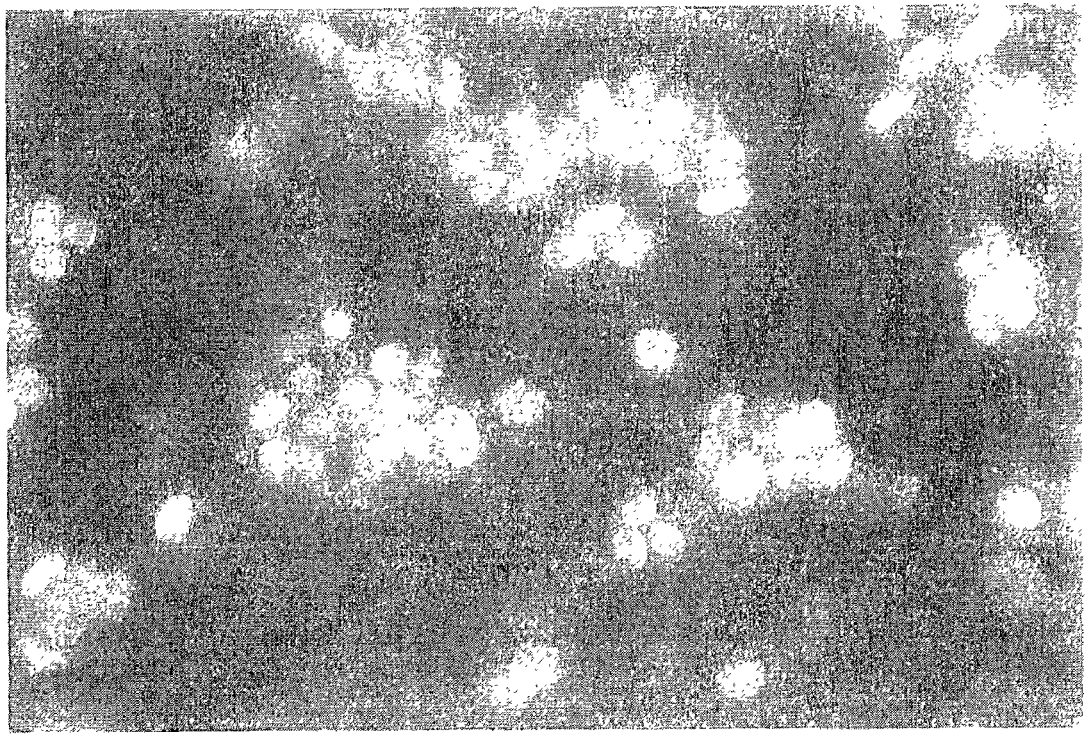
FIG. 15 shows a slide of HT-29 cells without Alpha 2-HS Glycoprotein (stained by Hoeschst dye).
Figure 16:
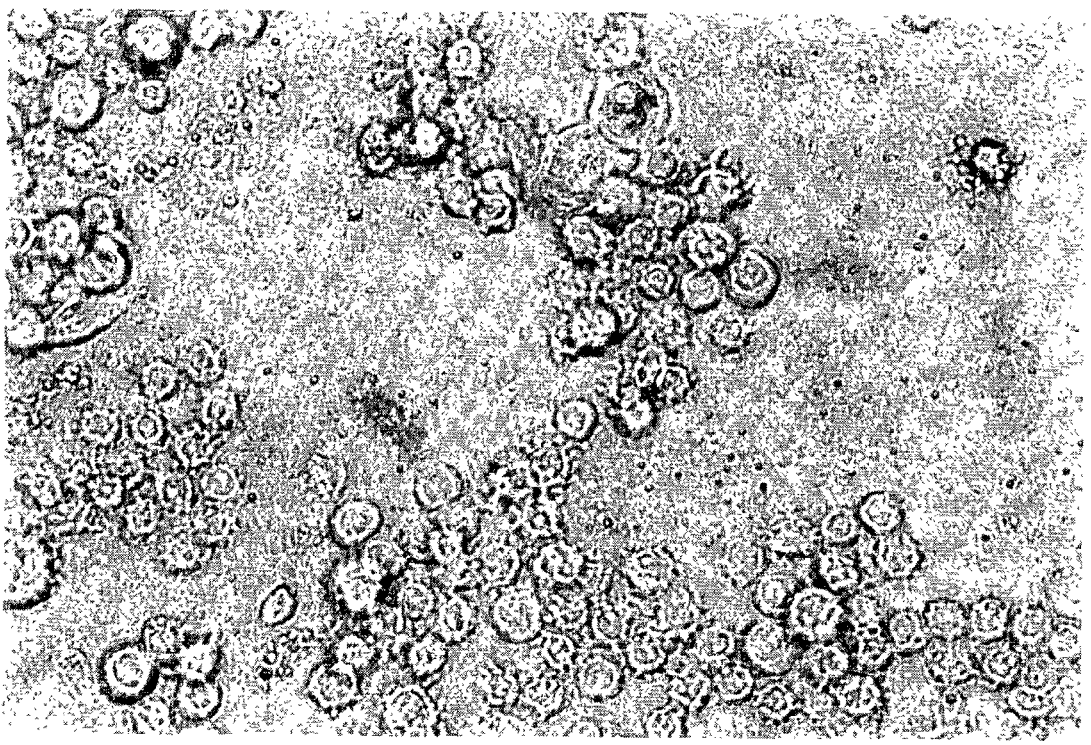
FIG. 16 shows another slide of HT-29 cells incubated with 5 μM Alpha 2-HS Glycoprotein for 4 hours (stained by Hoeschst dye).
Figure 17:
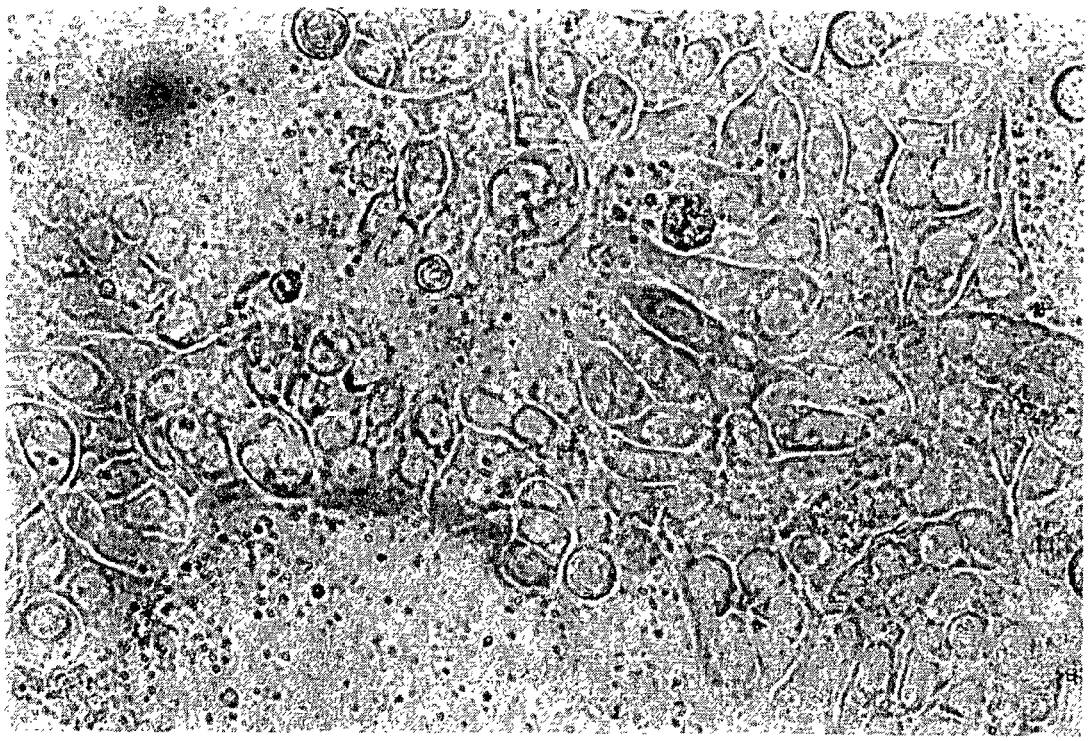
FIG. 17 shows another slide of HT-29 cells without Alhpha2.

9c. Supercharged Zinc Alpha2-HS Glycoprotein Induced Apoptosis in LNCaP, HT-29 And Hep G2 without Affecting CCD 18Co Supercharged zinc Alpha 2-HS glycoprotein induces apoptosis selectively. The morphological changes in HT-29 cancer cell lines due to apoptosis are shown in FIGS. 14 and 16. Incubation of HT-29 cells with supercharged zinc Alpha 2-HS glycoprotein (5 μM) resulted in the condensation and fragmentation of DNA (stained by Hoeschst dye), which are demonstrated by a more intense fluorescence and breakage of nuclei. As shown in FIG. 14, the nuclei of HT-29 cells incubated with 5 μM supercharged zinc Alpha 2-HS glycoprotein for 4 hours show a "crescent" shape. The DNA condensation, DNA fragmentation and peripheral crescents of the nuclei are characteristics of a cell under apoptosis. Apoptosis occurred in 90-95% of the HT-29 cells. This is in contrast to the control cells which were incubated with saline solution for four hours (stained by Hoeschst dye) in FIG. 15. FIG. 16 further shows the effects of incubating HT-29 cells with 5 μM supercharged zinc Alpha 2-HS glycoprotein over a period of 4 hours. The HT-29 cells demonstrate both cell shrinkage and cells round-up which are characteristics of apoptosis. This, again, is in stark contract to the control cells in FIG. 17.

Figure 18:
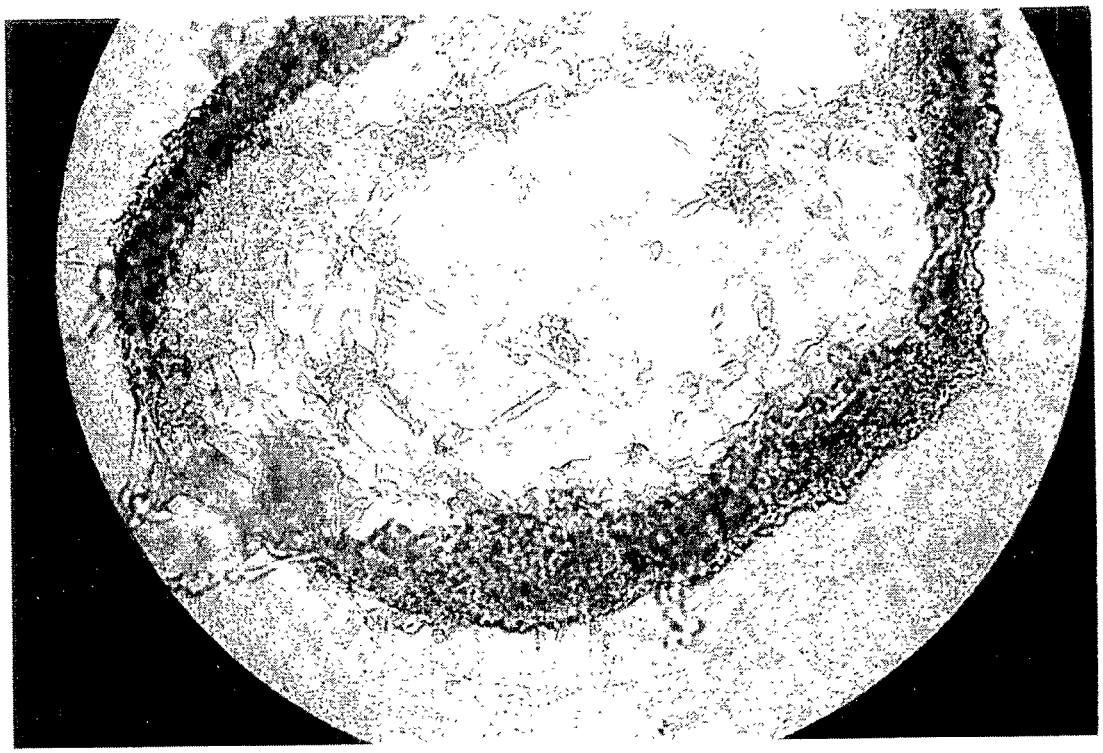
FIG. 18 shows a slide of LNCaP cells incubated with 5 μM Alpha 2-HS Glycoprotein for 4 hours.
Figure 19:
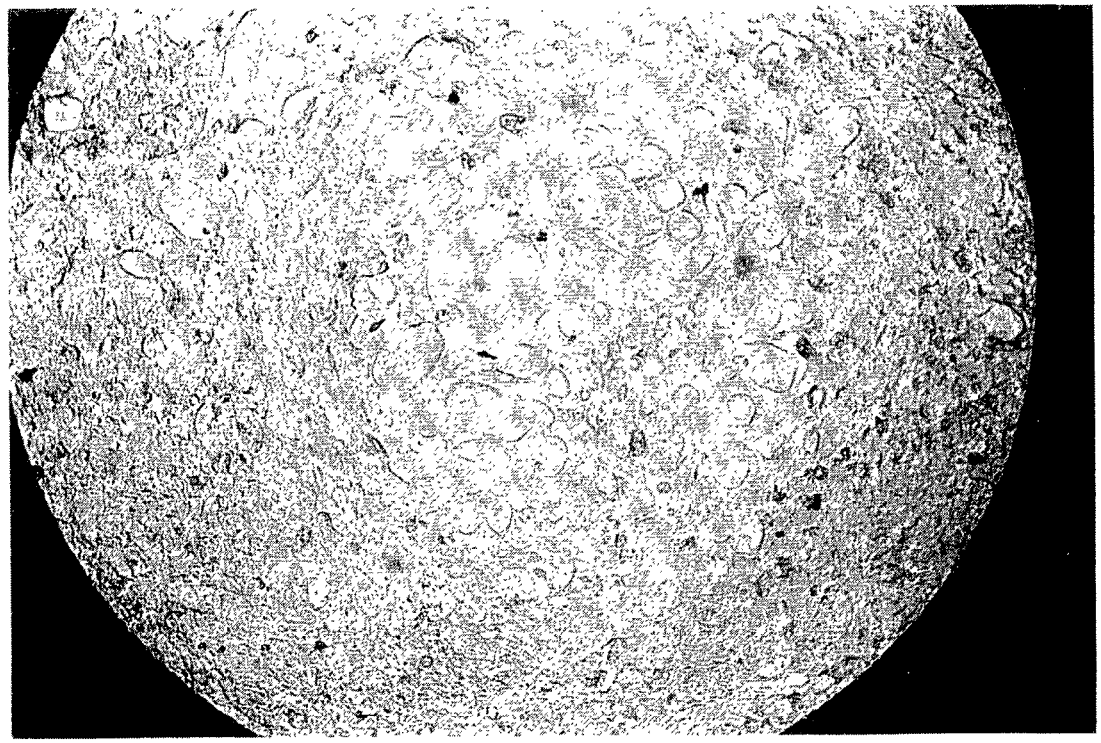
FIG. 19 shows a slide of LNCaP cells without Alpha 2-HS Glycoprotein.
Figure 20:
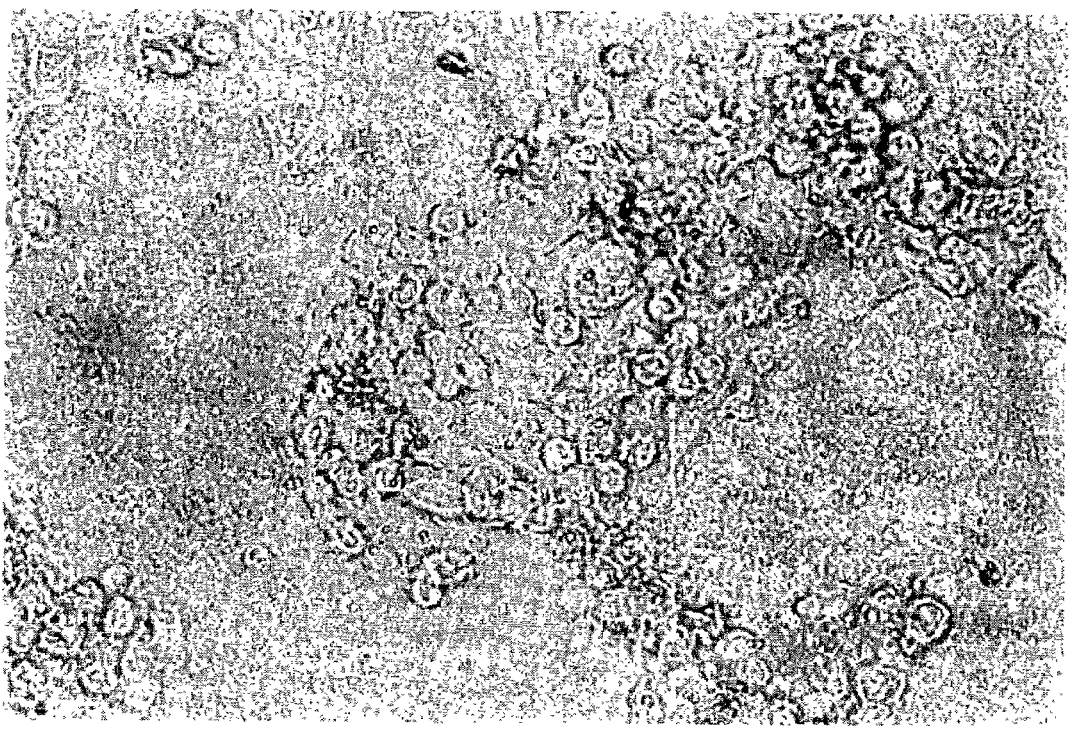
FIG. 20 shows a slide of Hep G2 cells incubated with 5 μM Alpha 2-HS Glycoprotein for 4 hours.
Figure 21:
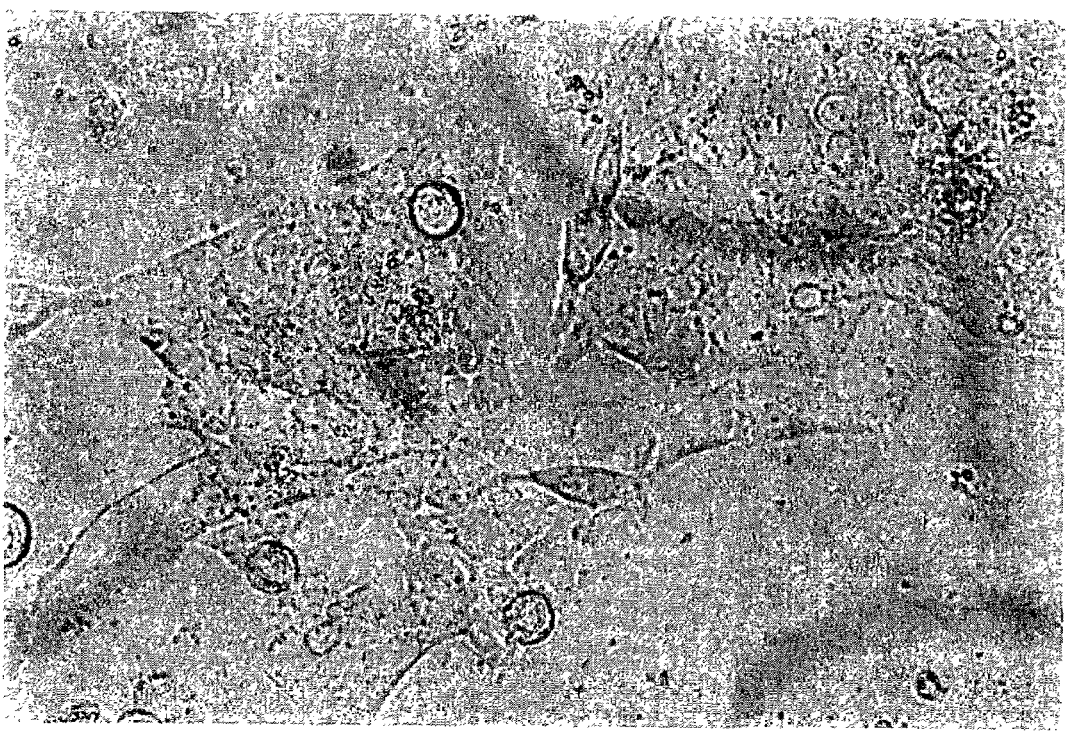
FIG. 21 shows a slide of Hep G2 cells without Alpha 2-HS Glycoprotein.

As shown in FIG. 18, incubation of 5 μM supercharged zinc Alpha 2-HS glycoprotein for 4 hours in LNCaP cells likewise resulted in 90-95% cell death as demonstrated by cell shrinkage and detachment versus the control cells in FIG. 19. In addition, as shown in FIG. 20, incubation of 5 μM supercharged zinc Alpha 2-HS glycoprotein for 4 hours in Hep G2 cells resulted in 90-95% cell death as demonstrated by cell shrinkage and cells round-up versus the control cells in FIG. 21.

9d. Supercharged Zinc Alpha 2-HS glycoprotein Does Not Affect CCD 18Co Cells

Figure 22:
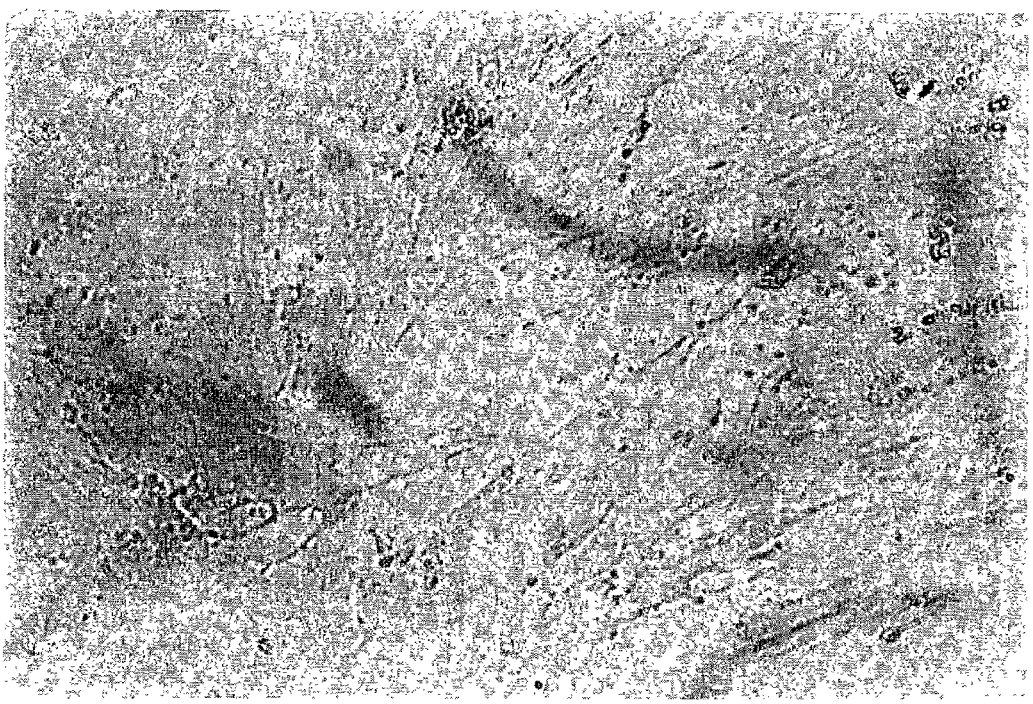
FIG. 22 shows a slide of CCD 18 Co cells incubated with 5 μM Alpha 2-HS Glycoprotein for 6 hours.
Figure 23:
FIG. 23 shows a slide of CCD 18 Co cells without Alpha 2-HS Glycoprotein.

Supercharged zinc Alpha 2-HS glycoprotein has no effect on CCD 18Co cells. Incubation of 5 μM supercharged zinc Alpha2 -HS glycoprotein in CCD 18Co cells for six hours did not cause cell death. As shown in FIG. 22, the cells are flat and healthy and could not be differentiated from those of the control in FIG. 23. Note that under the same conditions and concentrations of supercharged zinc alphs2-HS glycoprotein, apoptosis occurred in 90-95% of LNCaP, HT-29 and Hep G2 cells as demonstrated in Section 9c.

9e. Zinc is Necessary for Alpha 2-HS Glycoprotein to Induce Apoptosis

Pre-incubation of Alpha 2-HS glycoprotein with EDTA (without recharging with zinc) completely removed the apoptosis-inducing activity. HT-29 cells were incubated with 5 μM Alpha 2-HS glycoprotein (without zinc). After four hours, no apoptotic activity was seen. In addition, pre-incubation of Alpha 2-HS glycoprotein with EDTA and then recharging with calcium did not reveal any apoptosis-inducting activity. HT-29 cells were again incubated with 5 μM calcium charged Alpha 2-HS glycoprotein. After four hours, no apoptotic activity was seen, and the cells appeared normal and healthy. These results further demonstrate the importance that zinc plays in the selective apoptotic activity of Alpha2-HS glycoprotein.

9f. Supercharged Zinc Alpha 2-HS Glycoprotein Induced Apoptosis in a Dose Dependent Manner Supercharged zinc Alpha 2-HS glycoprotein induced apoptosis in a dose dependent manner. As the concentrations increased, so did the apoptotic affect. $LD_{50}$ at 6 hours were ascertained for HT-29, Hep G2, and LNCaP and are estimated to be 0.75 μM, 0.87 μM and 1.5 μM respectively.

9g. Supercharged Zinc Alpha 2-HS Glycoprotein Fragments also Selectively Induce Apoptosis When supercharged zinc Alpha 2-HS glycoprotein is dried under a vacuum, fragments are generated. (See Section 5a.) The dried fragments were reconstituted in 50 μl water. This fragment solution was passed through a molecular sieve membrane having a molecular weight cut-off of 10,000 Daltons. The resulting filtrate of fragments was collected and tested on cells in an apoptosis assay. This filtrate had an $LD_{50}$ at 6 hours on HT-29 cells of 0.7 μM.

As demonstrated herein, supercharged zinc Alpha 2-HS glycoprotein, along with active fragments of supercharged zinc Alpha 2-HS glycoprotein whether manufactured from modification of natural Alpha 2-HS glycoprotein, recombinantly, or synthetically, selectively induce apoptosis.

The scope of the subject invention includes not only the specific nucleotide sequences depicted herein, but all equivalent nucleotide sequences coding for molecules with substantially the same selective apoptotic activity.

I claim:

1. A method of inducing apoptosis in cancer cells, comprising the steps of supercharging Alpha 2-HS glycoprotein with zinc and administering said glycoprotein to the cancer cells.

2. The method of claim 1 further comprising the step of fragmenting said glycoprotein.

3. A method of inducing apoptosis in cancer cells, comprising the steps of fragmenting Alpha 2-HS glycoprotein, preselecting resulting fragments for apoptotic activity and administering said preselected fragments to the cancer cells.

* * * * *